US011724246B2

(12) United States Patent
Silvestre et al.

(10) Patent No.: US 11,724,246 B2
(45) Date of Patent: Aug. 15, 2023

(54) METHOD FOR PREPARING HIGHLY POROUS POLYMER PARTICLES FOR DIAGNOSTIC APPLICATIONS

(71) Applicant: Roche Diagnostics Operations, Inc., Indianapolis, IN (US)

(72) Inventors: Martin Eduardo Silvestre, Weilheim in Ob (DE); Stephan Hug, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 845 days.

(21) Appl. No.: 16/599,260

(22) Filed: Oct. 11, 2019

(65) Prior Publication Data
US 2020/0038839 A1 Feb. 6, 2020

Related U.S. Application Data

(63) Continuation of application No. PCT/EP2018/059384, filed on Apr. 12, 2018.

(30) Foreign Application Priority Data

Apr. 13, 2017 (EP) ..................... 17166492

(51) Int. Cl.
*B01J 20/26* (2006.01)
*B01J 20/28* (2006.01)
*B01J 20/32* (2006.01)
*B03C 1/01* (2006.01)
*G01N 33/543* (2006.01)

(52) U.S. Cl.
CPC ....... *B01J 20/28009* (2013.01); *B01J 20/267* (2013.01); *B01J 20/28059* (2013.01); *B01J 20/28061* (2013.01); *B01J 20/28064* (2013.01); *B01J 20/28066* (2013.01); *B01J 20/3234* (2013.01); *B01J 20/3272* (2013.01); *B01J 20/3282* (2013.01); *B01J 20/3293* (2013.01); *B03C 1/01* (2013.01); *G01N 33/54326* (2013.01); *B03C 2201/18* (2013.01); *B03C 2201/26* (2013.01)

(58) Field of Classification Search
CPC .... B01J 20/26; B01J 20/267; B01J 20/28059; B01J 20/28061; B01J 20/28066; B01J 20/3234; B01J 20/3272; B01J 20/3282; B01J 20/3293; B03C 1/01; B03C 2201/18; B03C 2201/26; G01N 33/54326
USPC ....................................... 502/406
See application file for complete search history.

(56) References Cited

U.S. PATENT DOCUMENTS 6,541,527 B1 4/2003 Ihm et al.
2003/0219597 A1 11/2003 Carr et al.

FOREIGN PATENT DOCUMENTS

| CN | 102786810 A | 11/2012 |
|---|---|---|
| EP | 2003455 A1 | 12/2008 |
| EP | 2015074 A1 | 1/2009 |
| EP | 2138229 A2 | 12/2009 |

OTHER PUBLICATIONS

Zhitao Wang et al., Cross-linking of polystyrene by Friedel Crafts chemistry to improve thermal stability, Polymer Degradation and Stability 64 (1999) pp. 387-395.
V. V. Tolmacheva et al., Magnetic Adsorbents Based on Iron Oxide Nanoparticles for the Extraction and Preconcentration of Organic Compounds, Journal of Analytical Chemistry, 2016, vol. 71, No. 4, pp. 321-338.
Ahn, Jou-Hyeon et al., Rapid Generation and Control of Microporosity, Bimodal Pore Size Distribution, and Surface Area in Davankov-Type Hyper-Cross-Linked Resins, Macromolecules, 2006, pp. 627-632, vol. 39.
Fontanals, N. et al., Hypercrosslinked materials; preparation, characterisation and applications, Polymer Chemistry, 2015, pp. 7231-7244, vol. 6.
Hütten, Andreas et al., New magnetic nanoparticles for biotechnology, Journal of Biotechnology, 2004, pp. 47-63, vol. 112.
International Search Report dated May 18, 2018, in Application No. PCT/EP2018/059384, 4 pp.
Jiang, Sai et al., Preparation of magnetically recyclable MIL-53(Al)@SiO2@Fe3O4 catalysts and their catalytic performance for Friedel-Crafts acylation reaction, Catalysis Today, 2016, pp. 83-90, vol. 264.
Liu, Jia et al., Highly Water-Dispersible Biocompatible Magnetite Particles with Low Cytotoxicity Stabilized by Citrate Groups, Angewandte Chemie, 2009, pp. 5875-5879, vol. 48.
Lu, An-Hui et al., Magnetic Nanoparticles: Synthesis, Protection, Functionalization, and Application, Angewandte Chemie International Edition, 2007, pp. 1222-1244, vol. 46.
Ma, Yan et al., Preparation of a novel magnetic microporous adsorbent and its adsorption behavior of p-nitrophenol and chlorotetracycline, Journal of Hazardous Materials, 2014, pp. 84-93, vol. 266.
Tan, Liangxiao and Tan, Bien, Hypercrosslinked porous polymer materials: design, synthesis, and applications, Chemical Society Reviews, 2017, pp. 3322-3356, vol. 46.

(Continued)

*Primary Examiner* — Edward M Johnson
(74) *Attorney, Agent, or Firm* — Stinson LLP

(57) ABSTRACT

A method of preparing a magnetic particle having a polymer matrix (P) and at least one magnetic core (M), preferably at least two magnetic cores (M), wherein the polymer matrix (P) comprises at least one hypercrosslinked polymer, wherein the method comprises (i) providing at least one magnetic core (M), preferably at least two magnetic cores (M), (ii) providing polymer precursor molecules, (iii) polymerizing the polymer precursor molecules according to (ii) in the presence of the at least one magnetic core (M), thereby forming a particle comprising the at least one magnetic core (M) is disclosed. Further, particles obtained or obtainable by this method as well as to the use of these particles are disclosed. In a further aspect, a method for determining at least one analyte in a fluid sample having the step of contacting of the magnetic particle with a fluid sample having or suspected of having the at least one analyte is disclosed.

9 Claims, 6 Drawing Sheets

(56) References Cited

OTHER PUBLICATIONS

Wang, Wei et al., Preparation of a permanent magnetic hypercrosslinked resin and assessment of its ability to remove organic micropollutants from drinking water, Frontiers of Environmental Science & Engineering, 2015, pp. 96-104, vol. 9, No. 1.

Xu, Shuai et al., Hierarchically structured porous organic polymer microspheres with built-in Fe3O4 supraparticles: construction of dual-level pores for Pt-catalyzed enantioselective hydrogenation, Polymer Chemistry, 2015, pp. 2892-2899, Abstract, vol. 6.

Yang, Xinjia et al., Magnetic microporous polymer nanoparticles, Polymer Chemistry, 2013, pp. 1425-1429, Abstract, vol. 4, No. 5.

METHOD FOR PREPARING HIGHLY POROUS POLYMER PARTICLES FOR DIAGNOSTIC APPLICATIONS

CROSS-REFERENCE TO RELATED APPLICATIONS

This application is a continuation of International Application No. PCT/EP2018/059384 filed Apr. 12, 2018, which claims priority to European Application No. 17166492.3 filed Apr. 13, 2017, the disclosures of which are hereby incorporated by reference in their entirey.

FIELD OF THE INVENTION

The present invention relates to a method of preparing a magnetic particle comprising a polymer matrix (P) and at least one magnetic core (M), preferably at least two magnetic cores (M), wherein the polymer matrix (P) comprises at least one hypercrosslinked polymer, wherein the method comprises (i) providing at least one magnetic core (M), preferably at least two magnetic cores (M), (ii) providing polymer precursor molecules, (iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and (iv) hypercrosslinking, the polymer matrix (P1) of the polymer particle obtained in (iii) via a Friedel-Crafts reaction, wherein the reaction is carried out at a temperature equal to or less than 80° C., to give the magnetic particle. Further, the present invention relates to particles obtained or obtainable by said method as well as to the use of these particles. In a further aspect, the invention relates to a method for determining at least one analyte in a fluid sample comprising the contacting of the magnetic particle with a fluid sample comprising or suspected to comprise the at least one analyte.

BACKGROUND

Magnetic particles are a great tool for capturing analytes from human samples. When e.g. covered with antibodies, these particles are able to specifically capture analytes which can be detected by optical techniques. The magnetic properties are of great importance as they allow easy, fast and cheap automation on diagnostic systems and additionally avoid time-consuming centrifugation and filtration steps. Here, superparamagnetic materials get more attention as they only show magnetization when an external magnetic field is applied. In the absence of an external magnetic field, magnetization appears to be zero (no "memory effect"). E.g. EP2003455A1 and EP2015074A1 describe the extraction of analytes from human samples by using magnetic particles on an LC/MS system.

High specific surface areas on the magnetic particles are required to enrich analytes from human samples. To increase the surface area to more than 1000 m$^2$/g, magnetic particles need to be coated with a porous matrix. This is usually done by embedding magnetic particles into a porous silica- or titanium oxide-matrix. One drawback is the high density of silica and titanium that leads to a decrease of magnetization with increasing film thickness. Furthermore, only mesoporous (pores >2 nm) systems can be developed by using silica or titanium oxide but especially for small analytes, materials with micropores (pores <2 nm) are preferred. Additionally, proteins and phospholipids are adsorbed into the large mesopores, which generates problematic matrix-effects in the LC/MS system.

One key requirement for the automation of the particles inside the enrichment-workflow-MS technology is a fast magnetic separation (<5 s) for high throughput. Particle size and saturation magnetization are crucial properties. Therefore, particles with high saturation magnetization (>5 A m$^2$ kg$^{-1}$) and large sizes (>2 µm) are required. Additionally, for the robustness of the system, carry-over of particles has to be avoided. Therefore, the particles need to have high magnetization and particle sizes larger than 1 µm.

Particles with polymer matrices, such as with polystyrene coatings, were suggested. Polystyrene networks can be formed by crosslinking polystyrene chains or styrenedivinylbenzene copolymers with the aid of crosslinking agents or by the copolymerization of styrene units with reactive groups, which can act as internal crosslinkers. Typical crosslinking agents are bischlorobenzyl compounds which react in the presence of FriedelCrafts catalysts with the aromatic backbone of the styrene chains forming crosslinking bridges. For internal crosslinking, usually vinylbenzyl-chloride is used as copolymer and crosslinked under Friedel-Crafts conditions as well. For the hypercrosslinking reaction the polystyrene polymers are typically swollen in dichloroethane and as Friedel-Crafts catalyst the Lewis acid FeCl$_3$ is used.

In particular, particles having a polymer matrix with micropores are described e.g. in Yang et al. *Polym. Chem.*, 2013, 4, 1425. According to Yang et al. iron oxide nanoparticles are first coated with oleic acid and are afterwards embedded into a polystyrene-matrix via a mini-emulsion polymerization. To reach a high specific surface area, the nanoparticles are finally hypercrosslinked by a Friedel-Crafts reaction, making use of FeCl$_3$ as a catalyst and dimethoxymethane as porosity dependent crosslinking reagent. The resulting particles have a size of 100 nm in average and a saturation magnetization of 4.1 A m$^2$ kg$^{-1}$. The particles are described as being useful for extracting organic molecules from water and also as drug carriers to control ibuprofen drug delivery, however, they display only a relatively small particle size as well as a low saturation magnetization which makes them disadvantageous for automation processes.

Xu et al. describes the synthesis of citrate-stabilized iron oxide nanoparticles with grain sizes of about 300 nm (S. Xu et al. *Polym. Chem.*, 2015, 6, 2892). These citrate-stabilized nanoparticles are coated with 3-(trimethoxysilyl) propyl methacrylate (MEMO) and covered with a polystyrol shell via a soap free emulsion polymerization. With this technique, one nanoparticle gets embedded into the polymer particle. In a second polymerization, another layer is formed on the particle. This polymerization is called a seeded swelling polymerization and contains a different monomer composition. As a last step, porosity is formed by a hypercrosslinking reaction with FeCl$_3$ as pore-forming catalyst. However, with this process only sizes of about 400 nm are reached with a saturation magnetization of 14.1 A m$^2$ kg$^{-1}$.

The reaction conditions used in the methods described in the prior are comparatively harsh, i.e. elevated temperatures, long reaction times and/or high concentrations of the Lewis acid are employed. The main side product of the Friedel-Crafts reaction under these conditions is HCl, which is often harmful for polymeric materials that contain magnetic components such as magnetite, i.e. the process is disadvantageous with respect to the final saturation magnetization of the particles.

Thus, there is still the need for an advantageous and mild method to prepare magnetic particles with a high saturation magnetization, which particles are useful for automation processes.

SUMMARY OF THE INVENTION

It is, therefore, an object of the present invention to provide porous magnetic particles with a relatively large particle size as well as a relatively high saturation magnetization. This problem is solved by the invention with the features of the independent patent claims. Advantageous developments of the invention, which can be realized individually or in combination, are presented in the dependent claims and/or in the following specification and detailed embodiments.

DETAILED DESCRIPTION OF THE INVENTION

Figure 1:
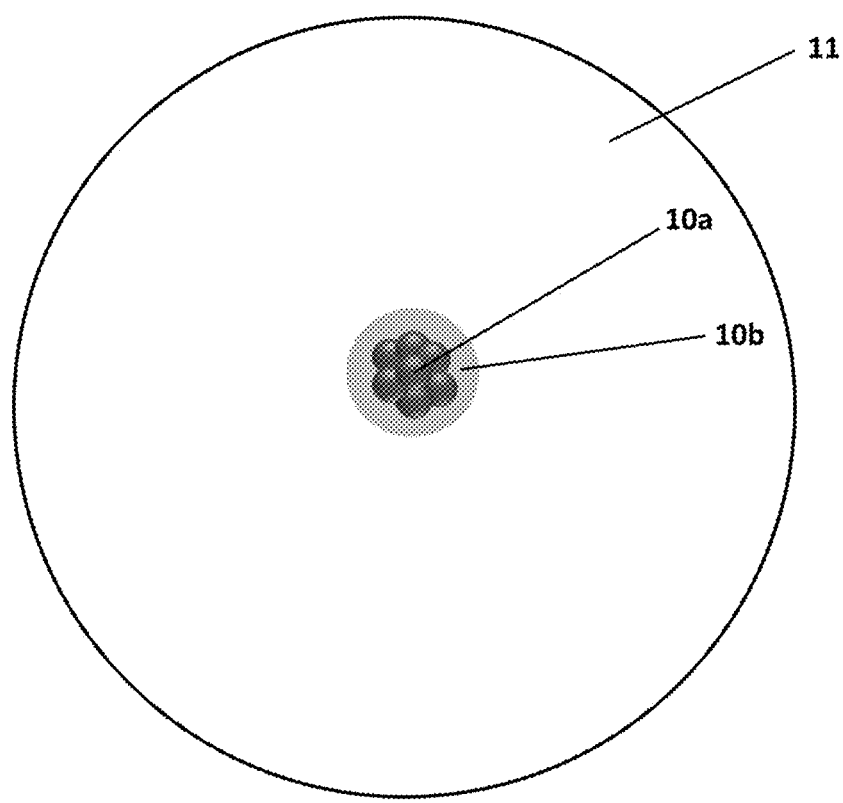
FIG. 1 is a schematic view of a magnetic particle comprising one magnetic core (M) (10a+10b) with 1-20 nanoparticles (10a), and a coating C1 (10b) as well as a polymer matrix (P) (11)
Figure 2:
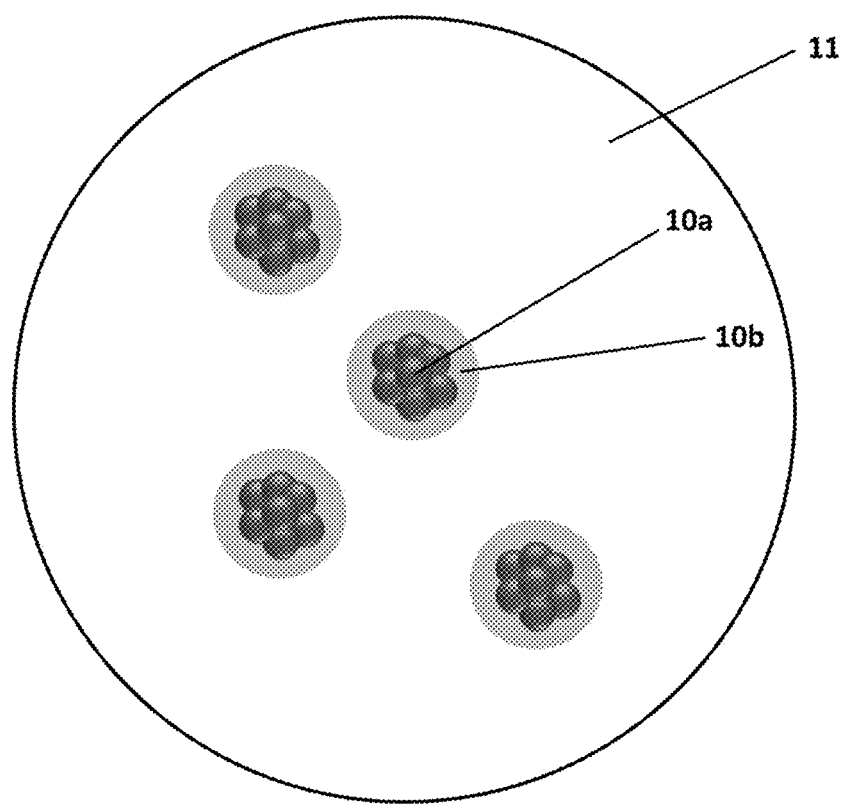
FIG. 2 is a schematic view of a more preferred magnetic particle comprising more than one, i.e. three magnetic cores (M) (10a+10b), each with 1-20 nanoparticles (10a) and a coating C1 (10b) as well as a polymer matrix (P) (11)
Figure 3:
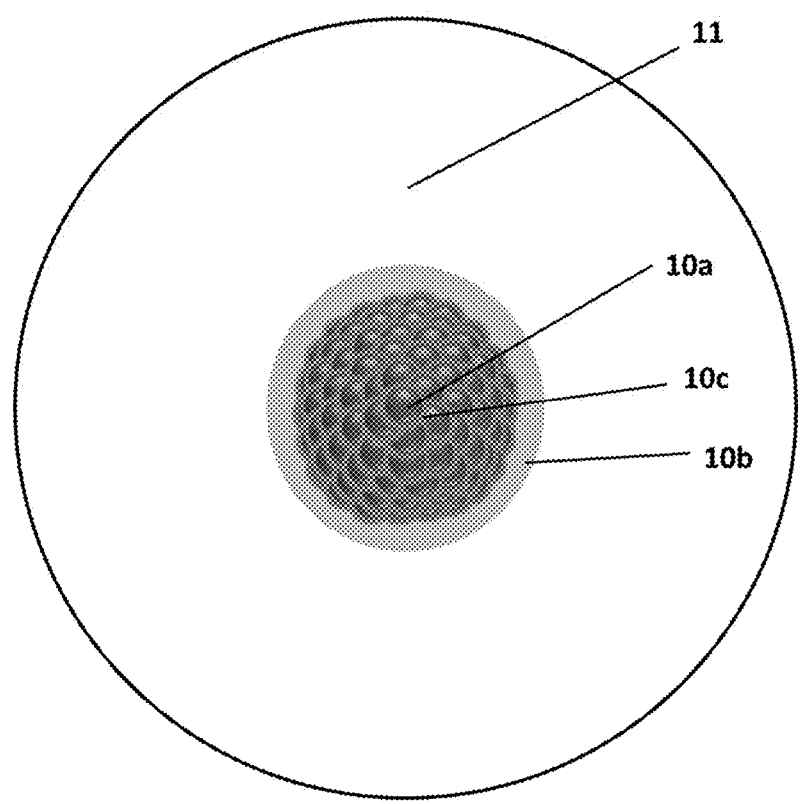
FIG. 3 is a schematic view of a magnetic particle with a polymer matrix (P) (11) and one magnetic core (M) consisting of a supraparticle formed upon aggregating of multiple nanoparticles (10a) which are coated with a coating C2 (10c), the magnetic core (M) further having a coating C1 (10b)
Figure 4:
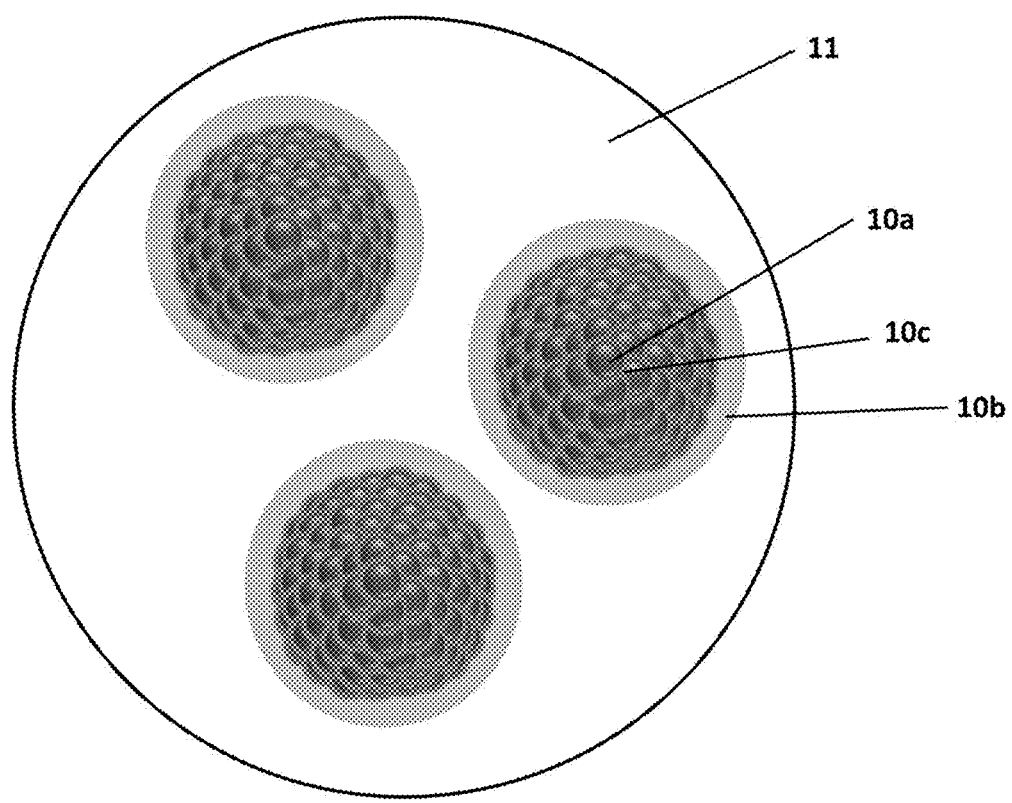
FIG. 4 is a schematic view of a more preferred magnetic particle with a polymer matrix (P) (11) and more than one magnetic core (M) consisting of a supraparticle formed upon aggregating of multiple nanoparticles (10a) which are coated with a coating C2 (10c), the magnetic core (M) further having a coating C1 (10b)

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once, typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such a way with other optional or non-optional features of the invention.

In a first aspect, the present invention relates to a method of preparing a magnetic particle comprising a polymer matrix (P) and at least one magnetic core (M), preferably at least two magnetic cores (M), wherein the polymer matrix (P) comprises at least one hypercrosslinked polymer, wherein the method comprises:

(i) providing at least one magnetic core (M), preferably at least two magnetic cores (M), (ii) providing polymer precursor molecules, (iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and (iv) hypercrosslinking the polymer matrix (P1) of the polymer particle obtained in (iii) via a Friedel-Crafts reaction, wherein the reaction is carried out at a temperature equal to or less than 80° C., to give the magnetic particle.

In a further aspect, the present invention is related to magnetic particles obtained or obtainable by said method.

In a third aspect, the present invention relates to the use of the particles obtained or obtainable by the method described above and below, for qualitative and/or quantitative determination of at least one analyte in a fluid.

Further, the present invention relates to a method for determining at least one analyte in a fluid sample comprising the contacting of a magnetic particle of the invention or a magnetic particle obtained by the method of the present invention with a fluid sample comprising or suspected to comprise the at least one analyte.

The Magnetic Particle

The magnetic particles according to the invention have a particle size in the range of from 1 to 60 micrometers, as determined according to ISO 13320. More preferably, the particle size is in the range of from 5 to 55 micrometers, more preferably in the range of from 10 to 50 micrometers, more preferably in the range of from 15 to 45 micrometers, more preferably in the range of from 20 to 40 micrometers, and in particular in the range of from 20 to 35 micrometers. According to one embodiment, the magnetic particles according to the invention have a particle size in the range of from 5 to 40 micrometers as determined according to ISO 13320.

As described above, the magnetic particle according to the invention comprises a polymer matrix (P) and at least one magnetic core (M). According to a preferred embodiment of the invention, the magnetic particle comprises more than one magnetic core (M), i.e. each particle preferably comprises at least one and, preferably, at least two magnetic cores (M). The magnetic core (M) comprises one or more magnetic nanoparticles, such as e.g. 1 to 20 magnetic nanoparticles, preferably 1 to 10, more preferably, 1 to 5 and most preferably 1 to 3 magnetic nanoparticles. Alternatively, it may comprise more than 20 nanoparticles and, preferably 100 to 1.5 million nanoparticles more preferably 750-750,000 nanoparticles, more preferably 1,750-320,000 nanoparticles, in particular 90,000-320,000 nanoparticles.

Thus, the present invention also relates to a magnetic particle as described above, as well as to a magnetic particle obtained or obtainable by the above-described method, wherein the particle comprises at least two magnetic cores (M). According to a particularly preferred embodiment, the magnetic particle, as well as to a magnetic particle obtained or obtainable by the above described method, consists of the at least two magnetic cores (M) and the polymer matrix (P).

Preferably the amount of magnetic cores (M) is chosen so that a desired saturation magnetization saturation of the final particle is achieved. Preferably, the magnetic particle according to the invention, or the particle obtained or obtainable by the above-described method, has a saturation magnetization of at least 1 A m$^2$/kg. Preferably, the saturation magnetization is at least 1 A m$^2$/kg, more preferably at least 2 A m$^2$/kg, more preferably at least 3 A m$^2$/kg, more preferably at least 4 A m$^2$/kg, more preferably at least 5 A m$^2$/kg, more preferably at least 6 A m$^2$/kg, more preferably at least 7 A m$^2$/kg, more preferably at least 8 A m$^2$/kg, more preferably at least 9 A m$^2$/kg, and in particular at least 10 A m$^2$/kg, such as in the range of from 10 A m$^2$/kg to 20 A m$^2$/kg, more preferably in the range of from 10 A m$^2$/kg to 30 A m$^2$/kg, as determined according to ASTM A 894/A 894M.

The particle of the present invention may, in principle, display any geometrical form, however, preferably, the particle is substantially spherical. As used herein, the term "substantially spherical" refers to particles with rounded shapes that are preferably non-faceted or substantially free of sharp corners. In certain embodiments, the substantially spherical particles typically have an average aspect ratio of less than 3:1 or 2:1, for example, an aspect ratio less than 1.5:1, or less than 1.2:1. In a certain embodiment, substantially spherical particles may have an aspect ratio of about 1:1. The aspect ratio ($A_R$) is defined as being a function of the largest diameter ($d_{max}$) and the smallest diameter ($d_{min}$) orthogonal to it ($A_R = d_{min}/d_{max}$). The diameters are determined via SEM or light microscope measurements.

The BET specific surface area of the magnetic particle as described above, as well as to a magnetic particle obtained or obtainable by the above-described method, is preferably in the range of from 50 to 2500 m$^2$/g, as determined according to ISO 9277. More preferably, the BET specific surface area of the magnetic particle is in the range of from 100 to 1500 m$^2$/g and in particular in the range of from 300 to 1000 m$^2$/g According to a preferred embodiment of the present invention, the magnetic particle as described above, as well as to a magnetic particle obtained or obtainable by the above described method, is superparamagnetic. The term "superparamagnetic" is known to the person skilled in the art and refers to the magnetic property encountered in particular for particles smaller than a single magnetic mono-domain. Such particles steadily orient upon applying an external magnetic field until a maximum value of the global magnetization, dubbed saturation magnetization, is reached. They relax when removing the magnetic field, with no magnetic hysteresis (no remanence) at room temperature. In the absence of an external magnetic field, superparamagnetic particles exhibit a non-permanent magnetic moment due to thermal fluctuations of the dipole orientation (Neel relaxation) and particle position (Brownian relaxation).

The Magnetic Core (M)

As described above, the magnetic particles according to the invention comprise at least one magnetic core (M) and preferably at least two magnetic cores (M). Preferably, the at least one magnetic core (M) comprises a compound selected from the group consisting of metal, metal carbide, metal nitride, metal sulfide, metal phosphide, metal oxide, metal chelate and a mixture of two or more thereof. The at least one magnetic core (M) may also comprise an alloy with a metal such as gold, silver, platinum or copper.

It is to be understood that each magnetic core (M) may comprise a mixture of two or more of the above-mentioned group, i.e. two or more of a metal, metal carbide, metal nitride, metal sulfide, metal phosphide, metal oxide, a metal chelate and a mixture of two or more thereof. Further, mixtures of two or more different metals, two or more different metal oxides, two or more different metal carbides, two or more different metal nitrides, two or more different metal sulphides, two or more different metal phosphides, two or more different metal chelates are conceivable.

Further, it is to be understood that in case the magnetic particle according to the invention comprises more than one magnetic core (M), each of the magnetic cores (M) present in a single particle may be the same or may differ from each other. Preferably, all magnetic cores (M) comprised in one magnetic particle are the same.

More preferably, the at least one magnetic core (M) comprises a metal oxide or a metal carbide.

In a preferred embodiment, the at least one magnetic core (M) comprises a metal, metal carbide, metal nitride, metal sulfide, metal phosphide, metal oxide, or metal chelate comprising at least one transition metal. Preferred transition metals according to the invention include, but are not limited to, chromium, manganese, iron, cobalt, nickel, zinc, cadmium, nickel, gadolinium, copper, and molybdenum. More preferably, the metal, metal carbide, metal nitride, metal sulfide, metal phosphide, metal oxide, or metal chelate comprises at least iron. More preferably, the at least one magnetic core (M) comprises an iron oxide, in particular an iron oxide selected from the group consisting of $Fe_3O_4$, $\alpha$-$Fe_2O_3$, $\gamma$-$Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3, more preferably 2, and wherein y is preferably 3 or 4. Most preferably, the at least one magnetic core (M) comprises $Fe_3O_4$.

Thus, the present invention also relates to a magnetic particle as described above, as well as to a magnetic particle obtained or obtainable by the above-described method, wherein the at least one magnetic core (M) comprises an iron oxide. Most preferably, the at least one magnetic core (M) comprises $Fe_3O_4$.

The magnetic core (M) preferably comprises, more preferably consists of nanoparticles and a coating C1.

Nanoparticles

The Nanoparticles are preferably the part which displays the magnetism, preferably superparamagnetism of a particle. Nanoparticles are sometimes also referred to as "magnetic nanoparticles" herein.

Preferably, the at least one nanoparticle comprises, preferably consists of, at least one magnetic, preferably superparamagnetic, nanoparticle and optionally one coating, such as a coating C2.

As used herein, the term "nanoparticle" refers to a particle being less than 100 nm in at least one dimension, i.e. having a diameter of less than 100 nm. Preferably, the nanoparticle according to the invention has a diameter in the range of from 1 to 20 nm, preferably 4 to 15 nm, as determined according to TEM-measurements. Thus, according to a preferred embodiment, the present invention also relates to a magnetic particle as described above, as well as to a magnetic particle obtained or obtainable by the above-described method, wherein the magnetic particle comprises at least one magnetic core (M) which comprises at least one nanoparticle and optionally one coating, such as a coating C2.

Each nanoparticle(s), preferably has/have a diameter in the range of from 1 to 20 nm, preferably 4 to 15 nm, as determined according to TEM-measurements. Preferably, the at least one magnetic nanoparticle is superparamagnetic.

The magnetic core (M) may comprise only one nanoparticle or more than one nanoparticle. In one embodiment, it comprises from 1 to 20 nanoparticles. In another embodiment, it comprises 100 to 1.5 million nanoparticles more preferably 750-750,000 nanoparticles, more preferably 1,750-320,000 nanoparticles, in particular 90,000-320,000 nanoparticles. The nanoparticles may be present as magnetic core in the form of individual (i.e. separate) particles or they may for aggregates consisting of several nanoparticles. Theses aggregates may have different sizes depending on the number of included nanoparticles. Typically, so called supraparticles are formed, which are described further below in more detail. In the case of a magnetic core comprising 100 or more nanoparticles, the nanoparticles typically form such supraparticles.

A Magnetic Core (M) Comprising 1-20 Nanoparticles

According to a first embodiment, the magnetic core (M) comprises, preferably consists of, 1-20 magnetic nanoparticles and optionally a coating C2, i.e. one magnetic nanoparticle, optionally with the coating C2, forms the nanoparticle of the magnetic core (M). Typically, the magnetic core comprises 1 to 20 magnetic nanoparticles, preferably 1 to 10, more preferably, 1 to 5 and most preferably 1 to 3 nanoparticles.

Preferably, in this case, the nanoparticle, comprises, more preferably consists of a compound selected from the group consisting of metal, metal carbide, metal nitride, metal sulfide, metal phosphide, metal oxide, metal chelate and a mixture of two or more thereof. It is to be understood that each nanoparticle may comprise, preferably consist of, a mixture of two or more of the above mentioned group, i.e. two or more of a metal, metal carbide, metal nitride, metal sulfide, metal phosphide, metal oxide, metal chelate and a mixture of two or more thereof. Further, mixtures of two or more different metals, two or more different metal oxides, two or more different metal carbides, two or more different metal nitrides, two or more different metal sulphides, two or more different metal chelates or two or more different metal phosphides are conceivable. More preferably, the nanoparticle comprises, more preferably consists of a metal oxide or a metal carbide. In a preferred embodiment, the metal is a transition metal. Preferred transition metals according to the invention include, but are not limited to, chromium, manganese, iron, cobalt, nickel, zinc, cadmium, nickel, gadolinium, copper, and molybdenum. Most preferably, the metal is iron.

Thus, according to a particularly preferred embodiment, the nanoparticle comprises, more preferably consists of a metal oxide, most preferably iron oxide, in particular $Fe_3O_4$.

According to this embodiment, it is preferred that in case more than one magnetic cores (M) are present in the magnetic particle, these magnetic cores (M) are not aggregated with each other. Preferably, these particles are substantially evenly distributed within the polymer matrix.

A Magnetic Core (M) Comprising a Supraparticle

According to a second preferred embodiment, the magnetic core (M) comprises more than 20 nanoparticles, and, typically more than 100 nanoparticles, wherein these nanoparticles are preferably aggregated with each other to form a supraparticle. More preferably, in this case, the magnetic core (M) comprises a supraparticle consisting of aggregated, coated, nanoparticles. Preferably, in this case, the magnetic core (M) comprises a supraparticle which comprises between 100 to 1.5 million nanoparticles more preferably 750-750,000 nanoparticles, more preferably 1,750-320,000 nanoparticles, in particular 90,000-320,000 nanoparticles. Preferably, each nanoparticle is coated with at least one coating C2. Preferably in this case, the magnetic core (M) thus comprises, preferably consists of, the supraparticle, which consist of, coated, nanoparticles being aggregated with each other, wherein the nanoparticles are coated with at least one coating C2, and wherein the coating is preferably deposited on the surface of the nanoparticles. The supraparticle may preferably also be coated with a coating C1.

Thus according to this second preferred embodiment of the invention, the magnetic particle according to the invention comprises more than 20 magnetic nanoparticles, and preferably 100 to 1.5 million nanoparticles, wherein said nanoparticles form at least one supraparticle. Each of the nanoparticles in the supraparticle is typically coated with at least one coating C2 and the supraparticle is typically coated with at least one coating C1.

Preferably, the coating C2 is a coating which covers at least a part, preferably the whole surface, of each nanoparticle. Preferably, also in this case, each nanoparticle comprises, more preferably consists of, a compound selected from the group consisting of metal, metal carbide, metal nitride, metal sulfide, metal phosphide, metal oxide, metal chelate and a mixture of two or more thereof. It is to be understood that each nanoparticle present in the supraparticle may comprise, preferably consist of, a mixture of two or more of the above-mentioned group, i.e. two or more of a metal, metal carbide, metal nitride, metal sulfide, metal phosphide, metal oxide, metal chelate and a mixture of two or more thereof. Further, mixtures of two or more different metals, two or more different metal oxides, two or more different metal carbides, two or more different metal nitrides, two or more different metal sulphides, two or more different metal chelates or two or more different metal phosphides are conceivable. More preferably, each nanoparticle in the supraparticle comprises, more preferably consists of, a metal oxide or a metal carbide. In a preferred embodiment, the metal is a transition metal. Preferred transition metals according to the invention include, but are not limited to, chromium, manganese, iron, cobalt, nickel, zinc, cadmium, nickel, gadolinium, copper, and molybdenum. Most preferably, the metal is iron.

According to a particularly preferred embodiment, each nanoparticle comprised in the supraparticle is a metal oxide nanoparticle, most preferably an iron oxide nanoparticle, in particular a $Fe_3O_4$-nanoparticle.

Thus, the present invention also relates to a magnetic particle as described above, as well as to a magnetic particle obtained or obtainable by the above described method, wherein the magnetic core (M) comprises or preferably consists of a supraparticle consisting of aggregated at least 20 magnetic nanoparticles wherein the nanoparticles are preferably being coated with at least one coating C2.

Preferably, the magnetic core (M) including the optional, at least one coating C1 has a diameter in the range of from 80 to 500 nm, more preferably 150 to 400 nm, and most preferably 200 to 300 nm, as determined according to DLS (ISO 22412).

The Coating C2

As coating C2, in general any coating known to those skilled in the art, is conceivable. Preferably, the coating C2 is, however, selected from at least one member of the group consisting of dicarboxylic acids, tricarboxylic acids, polyacrylic acid, amino acids, surfactants and fatty acids. It is to thus be understood that the aforementioned group includes salts and derivatives, such as esters and polymers, of the mentioned compounds. Thus, the coating C2 is preferably selected from at least one member of the group consisting of dicarboxylic acids, dicarboxylic acid salts, dicarboxylic acid derivatives, tricarboxylic acids, tricarboxylic acid salts, tricarboxylic derivatives, polyacrylic acid, polyacrylic acid salts, polyacrylic acid derivatives, amino acids, amino acid salts, amino acid derivatives, surfactants, salt of surfactants, fatty acids, fatty acid salts and fatty acid derivatives.

As used herein, the terms coated or coating are used to refer to the process of adsorption, van der Waals and/or non-polar group interactions (e.g., chemisorption or physical adsorption), or covalent binding of the magnetic nanoparticle or supraparticle core and the coating C2 or C1 or between two or more coatings, if present.

Preferably as fatty acids, fatty acid salts or fatty acid derivatives, such compounds are chosen which are capable of binding to the surface of the supraparticle, thereby preferably stabilizing the supraparticle. A fatty acid employed as coating C2 is preferably a single chain of alkyl groups containing from 8 to 22 carbon atoms with a terminal carboxyl group (—COOH) and high affinity adsorption (e.g., chemisorption or physical adsorption) to the surface of the magnetic particle. The fatty acid has multiple functions including protecting the magnetic particle core from oxidation and/or hydrolysis in the presence of water, which can significantly reduce the magnetization of the nanoparticle (Hutten, et al. (2004) J. Biotech. 112:47-63); stabilizing the nanoparticle core; and the like. The term "fatty acid" includes saturated or unsaturated, and in particular unsaturated fatty acids. Exemplary saturated fatty acids include lauric acid, myristic acid, palmitic acid, stearic acid, arachidic acid, propionic acid, butyric acid, valeric acid, caproic acid, enanthic acid, caprylic acid, pelargonic acid, capric acid, undecylic acid, tridecylic acid, pentadecylic acid, margaric acid, nonadecylic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid and octatriacontanoic acid and the like. Exemplary unsaturated fatty acids include oleic acid, linoleic acid, linolenic acid, arachidonic acid, hexadecatrienoic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, calendic acid, eicosadienoic acid, docosadienoic acid, adrenic acid, docosapentaenoic acid, tetracosatetraenoic acid, tetracosapentaenoic acid, 5-dodecenoic acid, 7-tetradecenoic acid, palmitoleic acid, vaccenic acid, paullinic acid, 15-docosenoic acid, 17-tetracosenoic acid, elaidic acid, gondoic acid, mead acid, erucic acid, nervonic acid, rumenic acid, calendic acid, jacaric acid, eleostearic acid, catalpic acid, punicic acid, rumelenic acid, parinaric acid, bosseopentaenoic acid, pinolenic acid, podocarpic acid and the like. The fatty acid can be synthetic or isolated from a natural source using established methods. Moreover, a fatty acid can be a derivative such as a fatty acid enol ester (i.e., a fatty acid reacted with the enolic form of acetone), a fatty ester (i.e., a fatty acid with the active hydrogen replaced by the alkyl group of a monohydric alcohol), a fatty amine or fatty amide, or in particular embodiments, a fatty alcohol as described above. A particularly preferred fatty acid is oleic acid.

A surfactant, as used in the context of the instant invention, is an organic compound that is amphipathic, i.e., containing both hydrophobic groups and hydrophilic groups. Preferably surfactants are chosen which are capable of binding to the surface of the supraparticle thereby preferably stabilizing the supraparticle surfactants with a variety of chain lengths, hydrophilic-lipophilic balance (HLB) values and surfaces charges can be employed depending upon the application. Preferably, the surfactant according to the invention is a quateranary ammonium salt, alkylbenzenesulfonates, lignin sulfonates, polyoxylethoxylate, or sulfate ester. Non-limiting examples of surfactants are cetyltrimethylammonium bromide, cetyltrimethylammonium chloride, nonyphenolpolyethoxylates (i.e. NP-4, NP-40 and NP-7), sodium dodecylbenzenesulfonate, ammonium lauryl sulfate, sodium laureth sulfate, sodium myreth sulfate, docusate, perfluorooctanesulfonate, perfluorobutanesulfonate, alkyl-aryl ether phosphates, alkyl ether phosphates, sodium stearate, 2-Acrylamido-2-methylpropane sulfonic acid, ammonium perfluorononanoate, magnesium laureth sulfate, perfluorononanoic acid, perfluorooctanoic acid, phospholipids, potassium lauryl sulfate, sodium alkyl sulfate, sodium dodecyl sulfate, sodium laurate, sodium lauroyl sarcosinate, sodium nonanoyloxybenzenesulfonate, sodium pareth sulfate, behentrimonium chloride, benzalkonium chloride, benzethonium chloride, bronidox, dimethyldioctadecylammonium bromide, dimethyldioctadecylammonium chloride, lauryl methyl gluceth-10 hydroxypropyl dimonium chloride, octenidine dihydrochloride, olaflur, N-oleyl-1,3-propanediamine, stearalkonium chloride, tetramethylammonium hydroxide, thonzonium bromide, cetomacrogol 1000, cetostearyl alcohol, cetyl alcohol, cocamide DEA, cocamide MEA, decyl polyglucose, disodium cocoamphodiacetate, glycerol monostearate, polyethylene glycol isocetyl ether, octylphenoxypolyethoxyethanol, lauryl glucoside, maltosides, monolaurin, mycosubtilin, nonoxynols, octaethylene glycol monododecyl ether, N-octyl beta-D-thioglucopyranoside, octyl glucoside, oleyl alcohol, pentaethylene glycol monododecyl ether, polidocanol, poloxamer, polyethoxylated tallow amine, polyglycerol polyricinoleate, polysorbate, sorbitan, sorbitan monolaurate, sorbitan monostearate, sorbitan tristearate, stearyl alcohol, surfactin, Triton X-100, Tween 80, cocamidopropyl betaine, cocamidopropyl hydroxysultaine, dipalmitoylphosphatidylcholine, hydroxysultaine, 1Lauryldimethylamine oxide, lecithin, myristamine oxide, peptitergents, sodium lauroamphoacetate and bis(2-ethylhexyl)sulfosuccinic ester.

The term "amino acids" as used within the meaning of the present invention refers to natural or unnatural amino acids or amino acid derivatives as well as to salts of amino acids. Preferably, amino acids are chosen which are capable of binding to the surface of the supraparticle thereby preferably stabilizing the supraparticle. Exemplary amino acids include cysteine, methionine, histidine, alanine, arginine, asparagine, aspartic acid, glutamic acid, glutamine, glycine, isoleucine, leucine, lysine, phenylalanine, proline, serine, threonine, tryptophan, tyrosine, valine, selenocysteine, pyrrolysine, cysteine, dehydroalanine, enduracididine, lanthionine, norvaline and derivatives thereof.

The term "dicarboxylic acid" within the meaning of the present invention refers to a hydrocarbon or substituted hydrocarbon containing two carboxylic acid functional groups (i.e., $R^1$—$(C(O)OH)_2$), where $R^1$ is (a) a linear hydrocarbon containing from 0-18 carbon units or (b) a cyclic hydrocarbon containing 3-8 carbon units, either as aromatic or non-aromatic rings. The term includes salts and derivatives of fatty acids, such as esters of fatty acids. Representative dicarboxylic acids are e.g. propanedioic acid, butanedioic acid, pentanedioic acid, hexanedioic acid, heptanedioic acid, octanedioic acid, nonanedioic acid, decanedioic acid, undecanedioic acid, dodecanedioic acid, hexadecanedioic acid, maleic acid, fumaric acid, glutaconic acid, traumatic acid, muconic acid, glutinic acid, citraconic acid, mesaconic acid, malic acid, aspartic acid, glutamic acid, tartronic acid, tartaric acid, diaminopimelic acid, saccharic acid, mesoxalic acid, oxaloacetic acid, acetonedicarboxylic acid, arabinaric acid, phthalic acid, isophthalic acid, terephthalic acid, diphenic acid, 2,6-naphthalenedicarboxylic acid.

The term "tricarboxylic acid" within the meaning of the present invention refers to a hydrocarbon or substituted hydrocarbon containing three carboxylic acid functional groups (i.e., $R^1$—$(C(O)OH)_3$), where $R^1$ is (a) a linear hydrocarbon containing from 3-18 carbon units or (b) a cyclic hydrocarbon containing 3-8 carbon units, either as aromatic or non-aromatic rings. The term includes salts and derivatives of fatty acids, such as esters of fatty acids. Representative tricarboxylic acids are e.g. citric acid (2-hydroxypropane-1,2,3 tricarboxylic acid), isocitric acid (1-hydroxypropane-1,2,3 tricarboxylic acid), aconitic acid (prop-1-ene-1,2,3 tricarboxylic acid), propane-1,2,3-tricarboxylic acid, trimellitic acid (benzene-1,2,4-tricarboxylic acid), trimesic acid (benzene-1,3,5-tricarboxylic acid), oxalosuccinic acid (1-oxopropane-1,2,3-tricarboxylic acid) or hemimellitic acid (benzene-1,2,3-tricarboxylic acid). Preferably, the tricarboxylic acid is citric acid including citrates, i.e. salts and derivatives of citric acid.

Preferably, C2 is selected from the group consisting of citric acid, histidine, CTAB, CTAC, sodium oleate, polyacrylic acid or mixtures of two or more thereof (including the respective salts or derivatives thereof). Thus, the present invention also relates to a magnetic particle as described above, as well as to a magnetic particle obtained or obtainable by the above-described method, wherein the magnetic core (M) preferably consists of, a supraparticle consisting of aggregated magnetic nanoparticles with at least one coating C2, wherein the at least one coating C2 is selected from the group consisting of citrate, histidine, CTAB, CTAC, sodium oleate, polyacrylic acid or mixtures of two or more thereof.

Preferably the amount of coating C2 is in the range of from 1 to 80% by weight, more preferably in the range of from 5 to 70% by weight, more preferably in the range of from 10 to 50% by weight, most preferably 20 to 40% based on the total weight of the sum of C2 and the supraparticle.

The Coating C1

As described above, the magnetic core (M), preferably comprises, more preferably consists of, magnetic nanoparticles and a coating C1. Thus, the present invention also relates to a magnetic particle as described above, as well as to a magnetic particle obtained or obtainable by the above-described method, wherein the at least one magnetic core (M) further comprises a coating C1.

The coating C1 is preferably deposited on the surface of the magnetic core (M). It is to be understood that between coating C1 and the magnetic core (M), further separating layers may exist, however, according to a preferred embodiment, C1 is coated directly on the magnetic core (M).

Preferably, the coating C1 surrounds the whole surface of the magnetic core (M). In principle, any suitable coating known to those skilled in the art may be employed. Preferably, the coating C1 is selected from the group consisting of tensides, silica, silicates, silanes, phosphates, phosphonates, phosphonic acids and mixtures of two or more thereof.

Thus, the present invention also relates to a magnetic particle as described above, as well as to a magnetic particle obtained or obtainable by the above-described method, comprising at least one magnetic core (M), wherein the at least one magnetic core (M) comprises at least one coating C1, and wherein the coating C1 is selected from the group consisting of tensides, silica, silicates, silanes, phosphates, phosphonates, phosphonic acids and mixtures of two or more thereof.

Preferably, the coating C1 is selected from the group consisting of silica, tetraethyl orthosilicate, 3-(trimethoxysilyl)propyl methacrylate, vinyltrimethoxysilane, vinyltriethoxysilane, allyltrimethoxysilane, allyltriethoxysilane, triethoxyvinylsilane, 3-(trimethoxysilyl)propyl acrylate, trimethoxy(7-octen-1-yl)silane, trimethoxymethylsilane, triethoxymethylsilane, ethyltrimethoxysilane, triethoxy(ethyl) silane, trimethoxyphenylsilane, trimethoxy(2-phenylethyl) silane trimethoxy(propyl)silane, n-propyltriethoxysilane, isobutyl(trimethoxy)silane, isobutyltriethoxysilane, vinylphosphonic acid, dimethyl vinylphosphonate, diethyl vinylphosphonate, diethyl allylphosphonate, diethyl allyl phosphate, diethyl (2-methylallyl)phosphonate, octylphosphonic acid, butylphosphonic acid, decylphosphonic acid, hexylphosphonic acid, hexadecylphosphonic acid, n-dodecylphosphonic acid, lauric acid, myristic acid, palmitic acid, stearic acid, and arachidic acid, propionic acid, butyric acid, valeric acid, caproic acid, enanthic acid, caprylic acid, pelargonic acid, capric acid, undecylic acid, tridecylic acid, pentadecylic acid, margaric acid, nonadecylic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, oleic acid, linoleic acid, linolenic acid, arachidonic acid, hexadecatrienoic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, calendic acid, eicosadienoic acid, docosadienoic acid, adrenic acid, docosapentaenoic acid, tetraco-satetraenoic acid, tetracosapentaenoic acid, 5-dodecenoic acid, 7-tetradecenoic acid, pal-mitoleic acid, vaccenic acid, paullinic acid, 15-docosenoic acid, 17-tetracosenoic acid, elaidic acid, gondoic acid, mead acid, erucic acid, nervonic acid, rumenic acid, calendic acid, jacaric acid, eleostearic acid, catalpic acid, punicic acid, rumelenic acid, parinaric acid, bosseopentaenoic acid, pinolenic acid, podocarpic acid and mixtures of two or more thereof.

Preferably, each magnetic core (M) comprises the coating C1 in an amount of from 1 to 40% by weight, preferably from 2 to 15% by weight, more preferably from 5 to 10% by weight, based on the total weight of at least one magnetic core (M).

According to one preferred embodiment of the invention, the coating C1 comprises vinyl or acryl groups.

The Polymer Matrix (P)

As described above, each particle comprises besides the at least one magnetic core (M) a polymer matrix (P).

Preferably, the polymer matrix (P) is a porous polymer matrix, preferably a porous polymer matrix comprising pores having a pore size smaller than 100 nm, more preferably smaller than 100 nm, more preferably smaller than 90 nm, more preferably smaller than 80 nm, more preferably smaller than 70 nm, more preferably smaller than 60 nm, more preferably smaller or equal to 50 nm, such as in the range of from 0.5 nm to 50 nm, preferably in the range of from 1 to 20 nm as determined according to ISO 15901.

Thus, the present invention also relates to a magnetic particle as described above, as well as to a magnetic particle obtained or obtainable by the above-described method, wherein the polymer matrix (P) is a porous polymer matrix comprising pores having a pore size smaller than 100 nm, preferably smaller or equal to 50 nm, as determined according to ISO 15901.

Preferably at least 90% of all pores present in the polymer matrix have a pore size smaller than 10 nm and at least 50% of all pores present in the polymer matrix have a pore size smaller than 5 nm, as determined according to ISO 15901.

According to a particularly preferred embodiment, the polymer matrix does not comprise macropores, i.e. pores having a pore size larger than 50 nm.

Preferably, the particle comprises the polymer matrix (P) in an amount in the range of from 40 to 98% by weight, more preferably in the range of from 50 to 95% by weight, more preferably in the range of from 60 to 90% by weight, and most preferably in the range of from 70 to 85% by weight, based on the total weight of the particle.

The polymer matrix (P) preferably comprises a co-polymer obtained or obtainable by a method comprising a polymerization of at least two different monomeric building blocks selected from the group consisting of styrene, functionalized styrenes, vinylbenzylchloride, divinylbenzene, vinylacetate, methylmethaacrylate and acrylic acid. Preferably, the co-polymer obtained or obtainable by a method comprising a polymerization of at least two different monomeric building blocks selected from the group consisting of the following monomers:

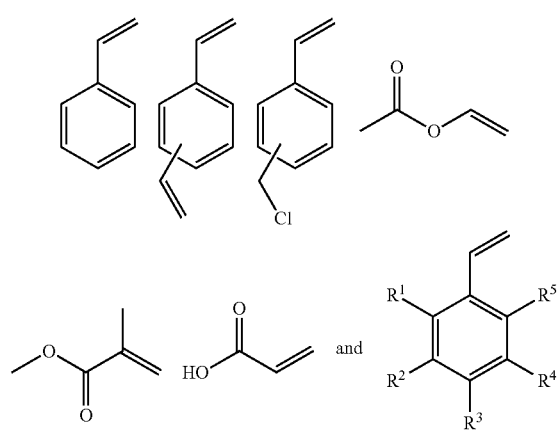

with $R^1$, $R^2$, $R^3$, $R^4$ and $R^5$, are, independently of each other selected from the group consisting of —$N_3$, —$NH_2$, —Br, —I, —F, —NR'R'', —NR'R''R''', —COOH, —CN, —OH, —OR', —COOR', —NO2, —SH2, —SO2, —R'(OH)x, —R'(COOH)x, —R'(COOR'')x, —R'(OR'')x, —R'(NH2)x, —R'(NHR'')x, —R'(NR''R''')x, —R' (Cl)x, —R'(I)x, —R' (Br)x, —R'(F)x, R'(CN)x, —R'(N3)x, —R'(NO2)x, —R' (SH2)x, —R'(SO2)x, alkyl, aryl, cycloalkyl, heteroaryl, heterocycloalkyl and with R', R'' and R''' being, independently of each other, selected from the group consisting of alkyl, aryl, cycloalkyl, heteroaryl, heterocycloalkyl, halides, hydrogen, sulfides, nitrates and amines, and wherein x is an integer in the range of from 1 to 3.

In principle any polymer known to those skilled in the art may be employed. Preferably, the polymer matrix comprises a crosslinked polymer, this polymer more preferably being obtained or obtainable by a method comprising co-polymerizing suitable monomeric building blocks in the presence of at least one monomeric building block which is a crosslinking agent, thus an agent with which in the resulting polymer a crosslinking is achieved. Suitable agents for crosslinking polymers are known to those skilled in the art, and include, but are not limited to building block such as divinylbenzene, bis(vinylphenyl)ethane, bis(vinylbenzyloxy)hexane, bis(vinylbenzyloxy)dodecane and derivatives of those.

According to a particularly preferred embodiment divinylbenzene is employed as crosslinking agent.

Preferably, the polymer matrix is obtained or obtainable by a method comprising co-polymerizing monomeric building blocks, wherein 5-90 vol % of all monomeric building blocks are crosslinking agents.

Preferably, in the resulting polymer a crosslinking degree of at least 5% is obtained.

The at least one magnetic core (M) is preferably embedded in the polymer matrix. The term "embedded" in this context is denoted to mean the magnetic core is, preferably, fully surrounded by the polymer matrix. Alternatively, the magnetic core may be partially surrounded by the polymer matrix. In this case, however, the magnetic core shall be immobilized within the particle.

As described above, according to a preferred embodiment, the particle comprises at least two magnetic cores (M). In this case, it is to be understood, that each magnetic core (M) present in the particle is embedded in the polymer matrix (P). Thus, the present invention also relates to a magnetic particle as described above, as well as to a magnetic particle obtained or obtainable by the above-described method, wherein the at least two magnetic cores (M) are embedded in the polymer matrix.

Hypercrosslinking

More preferably, the polymer matrix P comprises a crosslinked co-polymer obtained or obtainable by a method comprising the polymerization of at least two different monomeric building blocks as described above, whereby preferably a crosslinked polymer is obtained, wherein the crosslinked polymer is further hypercrosslinked. Thus, more preferably, the polymer matrix comprises, in particular consists of a hypercrosslinked polymer.

The term "hypercrosslinked" as used herein refers to a type of multiple crosslinking resulting in a rigid three-dimensional network. Preferably, the hypercrosslinking is achieved by subjecting the crosslinked polymer to a chemical reaction, thereby obtaining the hypercrosslinked polymer. Thus, the polymer matrix (P) is a polymer matrix being obtained or obtainable by further hypercrosslinking the polymer with or without a hypercrosslinking agent by a chemical reaction. Suitable agents for hypercrosslinking polymers are known to those skilled in the art, and include, but are not limited to dichloroethane, dichloromethane, chloroform, carbon tetrachloride, dichlorobenzenes, trichlorobenzenes, dichloroalkanes, dibromoalkanes, diiodoalkanes, trichloroalkanes, tribromoalkanes, triiodoalkanes, dimethoxymethane, dimethoxyethane and mixtures of two or more thereof.

Preferably, the hypercrosslinking is achieved by subjecting the crosslinked polymer matrix to a Friedel-Crafts reaction, in particular to a Friedel Crafts reaction as described hereinunder.

Surface Functionalization

It is to be understood that the magnetic particles, comprising the at least one magnetic core M and the polymer matrix (P), may further comprise a surface modification. The surface of the particle, thus the surface of the polymer matrix (P) is preferably functionalized with at least one group selected from the group consisting of —OH, —COOH, diethylaminoethanol, R—SO$_2$—OH, —NH$_2$, R—SO$_2$—OH, —RNH, —R$_2$N, —R$_3$N$^+$—CH$_3$, —C$_2$H$_5$, —C$_4$H$_9$, —C$_{18}$H$_{37}$, —C$_6$H$_5$, —C$_6$H$_9$NO$_6$, Phenyl-Hexyl, Bi-Phenyl, Hydroxyapatit, boronic acid, biotin, azide, epoxide, alkyl, aryl, cycloalkyl, heteroaryl, heterocycloalkyl, aminoacids, —COOR, —COR, —OR, antibodies and fragments thereof, aptameres, nucleic acids, and receptor proteins or binding domains thereof. Preferably, these groups are being covalently attached to suitable functional groups of the polymer matrix. Ways to carry out such modifications are known to those skilled in the art.

Step (i)

As described above, the at least one magnetic core (M) preferably comprises a compound selected from the group consisting of metal, metal carbide, metal nitride, metal sulfide, metal phosphide, metal oxide, metal chelate and a mixture of two or more thereof. The at least one magnetic core (M) may also comprise an alloy with a metal such as gold, silver, platinum, or copper. More preferably, the at least one magnetic core (M) comprises a metal oxide or a metal carbide, more preferably, the at least one magnetic core (M) comprises an iron oxide, in particular an iron oxide selected from the group consisting of Fe$_3$O$_4$, α-Fe$_2$O$_3$, γ-Fe$_2$O$_3$, MnFe$_x$O$_y$, CoFe$_x$O$_y$, NiFe$_x$O$_y$, CuFe$_x$O$_y$, ZnFe$_x$O$_y$, CdFe$_x$O$_y$, BaFe$_x$O and SrFe$_x$O, wherein x and y vary depending on the method of synthesis, and wherein x is preferably an integer of from 1 to 3, more preferably 2, and wherein y is preferably 3 or 4, and most preferably, the at least one magnetic core (M) comprises Fe$_3$O$_4$.

Thus, the present invention also relates to a method, as described above, and a magnetic particle obtained or obtainable by said method, wherein the at least one magnetic core (M comprises a metal oxide or a metal carbide, more preferably, the at least one magnetic core (M) comprises an iron oxide, in particular an iron oxide selected from the group consisting of Fe$_3$O$_4$, α-Fe$_2$O$_3$, γ-Fe$_2$O$_3$, MnFe$_x$O$_y$, CoFe$_x$O$_y$, NiFe$_x$O$_y$, CuFe$_x$O$_y$, ZnFe$_x$O$_y$, CdFe$_x$O$_y$, BaFe$_x$O and SrFe$_x$O, wherein x and y vary depending on the method of synthesis, and wherein x is preferably an integer of from 1 to 3, more preferably 2, and wherein y is preferably 3 or 4, and most preferably, the at least one magnetic core (M) comprises Fe$_3$O$_4$.

As described above, the magnetic core (M) preferably comprises, more preferably consists of, magnetic nanoparticles and a coating C1.

Preferably, step (i) comprises:
(i.1) providing at least one magnetic nanoparticle, and
(i.2) coating the at least one magnetic nanoparticle with a coating C1, the coating C1 preferably being selected from a group consisting of tensides, silica, silicates, silanes, phosphates, phosphonates, phosphonic acids and mixtures of two or more thereof to give the magnetic core (M).

The magnetic nanoparticle in (i.1), comprises, preferably consists of, at least one magnetic, preferably superparamagnetic, nanoparticle and optionally a coating C2.

Thus, step (i.1) comprises the provision of at least one nanoparticle.

Methods to provide magnetic nanoparticles are known to the skilled person and are e.g. described in Lu, Salabas, Schüth, Angew. Chem Int. Ed. 2007, 46, 1222-1244, the respective contents of which are hereby incorporated by reference.

In particular, in case of Fe$_3$O$_4$ nanoparticles, Fe(II) and Fe(III), oxide is precipitated from an aqueous, preferably from alkaline aqueous, media to give the respective nanoparticle.

According to the first preferred embodiment, described above, wherein each magnetic core (M) comprises at least one magnetic nanoparticle, optionally with a coating C1, step (i.1) thus comprises the provision of at least one magnetic nanoparticle, optionally with a coating C1, forming the magnetic core (M). Preferably, in this case, the magnetic nanoparticle does not comprise a coating C2. According to this first preferred embodiment of the invention, the magnetic particles according to the invention comprise preferably of from 1 to 20 magnetic nanoparticles.

According to this embodiment, it is preferred that in case more than one magnetic cores (M) are present in the magnetic particle, these magnetic cores (M) are not aggregated with each other. Preferably, these particles are substantially evenly distributed within the polymer matrix.

Thus, the present invention also relates to a method, as described above, as well as to a magnetic particle, as described above, wherein step (i) comprises:
(i.1) providing at least one magnetic nanoparticle optionally with a coating C2, to give the at least one magnetic nanoparticle, and
(i.2) coating the at least one magnetic nanoparticle with a coating C1, the coating C1 preferably being selected from the group consisting of tensides, silica, silicates, silanes, phosphates, phosphonates, phosphonic acids and mixtures of two or more thereof to give the magnetic core (M).

According to the second preferred embodiment described above, the magnetic core (M), i.e. preferably each magnetic core (M), comprises more than 20 nanoparticles, preferably, between 100 to 1.5 million nanoparticles more preferably 750-750,000 nanoparticles, more preferably 1,750-320,000 nanoparticles, in particular 90,000-320,000 nanoparticles. More preferably, the nanoparticles form at least one supraparticle consisting of aggregated, coated, nanoparticles. Preferably, said supraparticle being coated with at least one coating C1. Preferably in this case, the supraparticle is coated with at least one coating C1, wherein the coating is preferably deposited on the surface of the supraparticle. Thus, the supraparticle is preferably coated with a coating C1. It is to be understood that each nanoparticle within the supraparticle is preferably coated, such as with a coating C2. Step (i.1) thus comprises the provision of more than 20 nanoparticles, wherein the method further comprises aggregating said nanoparticles thereby forming at least one supraparticle and optionally coating each supraparticle with at least one coating C1.

Thus, the present invention also relates to a method, as described above, as well as to a magnetic particle, as described above, wherein step (i) comprises:

(i.1) providing at least one supraparticle by
 (i.1.1) providing more than 20 nanoparticles, preferably with a coating C2,
 (i.1.2) aggregating said nanoparticles, thereby forming a supraparticle, and
(i.2) coating the at least one supraparticle with a coating C1, the coating C1 preferably being selected from the group consisting of tensides, silica, silicates, silanes, phosphates, phosphonates, phosphonic acids and mixtures of two or more thereof to give the magnetic core (M).

In this case, each magnetic core (M) comprises a supraparticle preferably consisting of at least 21, coated, nanoparticles, preferably of 100 to 1.5 million nanoparticles more preferably of 750-750,000 nanoparticles, more preferably of 1,750-320,000 nanoparticles, in particular of 90,000-320,000, coated, nanoparticles being aggregated with each other.

It is to be understood that (i.1.1) and (i.1.2) may be carried out in a single step that is via a reaction in which supraparticles are directly provided.

Methods to provide supraparticles are known to the skilled person and are e.g. described in Liu et al., Angew. Chem. Int. Ed. 2009, 48, 5875-5879, the respective contents of which are hereby incorporated by reference.

In particular, in case of supraparticles comprising $Fe_3O_4$ nanoparticles the synthesis may comprise the partial reduction of $FeCl_3$, preferably at elevated temperatures, such as at a temperature in the range of from 150° C. to 250° C., and preferably at an increased pressure, such as a pressure of 2-10 bar, to obtain $Fe_3O_4$-supraparticles.

As described above, the coating C2 is thereby selected from at least one member of the group consisting of dicarboxylic acids, dicarboxylic acid salts, dicarboxylic acid derivatives, polyacrylic acid, polyacrylic acid salts, polyacrylic acid derivatives, tricarboxylic acids, tricarboxylic acid salts, tricarboxylic derivatives, amino acids, amino acid salts, amino acid derivatives, surfactants, salt of surfactants, fatty acids, fatty acid salts and fatty acid derivatives.

Methods to coat nanoparticles or supraparticles are known to the skilled person. The coating is preferably carried in situ during the synthesis of the supraparticle.

Step (ii)

In step (ii) polymer precursor molecules are provided, i.e. monomeric building blocks which after polymerization give the respective polymer are provided.

Preferably, these polymer precursor molecules in (ii) are selected from the group consisting of styrene, functionalized styrenes, vinylbenzylchloride, divinylbenzene, vinylacetate, methylmethaacrylate and acrylic acid, more preferably selected from the group consisting of the following monomers:

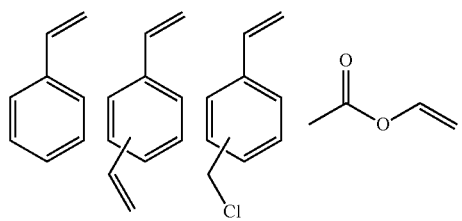

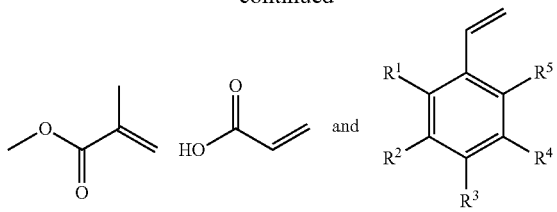

with $R^1$, $R^2$, $R^3$, $R^4$ and $R^5$, are, independently of each other selected from the group consisting of —$N_3$, —$NH_2$, —Br, —I, —F, —NR'R'', —NR'R''R''', —COOH, —CN, —OH, —OR', —COOR', —$NO_2$, —SH2, —$SO_2$, —R'(OH)$_x$, —R'(COOH)$_x$, —R'(COOR'')$_x$, —R'(OR'')$_x$, —R'($NH_2$)$_x$, —R'(NR''R''')$_x$, —R'(C1)$_x$, —R'(Br)$_x$, —R'(F)$_x$, R'(CN)$_x$, —R'($N_3$)$_x$, —R'($NO_2$)$_x$, —R'($SH_2$)$_x$, —R'($SO_2$)$_x$, alkyl, aryl, cycloalkyl, heteroaryl, heterocycloalkyl and with R', R'' and R''' being, independently of each other, selected from the group consisting of alkyl, aryl, cycloalkyl, heteroaryl, heterocycloalkyl, halides, hydrogen, sulfides, nitrates and amines.

Step (iii)

In step (iii), the polymer precursor molecules according to (ii) are polymerized in the presence of the at least one magnetic core (M), thereby forming a particle comprising the at least one magnetic core (M), preferably the at least two magnetic cores (M), embedded in a polymer matrix (P1), wherein the polymer matrix (P1) preferably comprises, more preferably consists of, a crosslinked polymer, as described above and below. This crosslinked polymer matrix P1 is then preferably further hypercrosslinked in step (iv) to give the polymer matrix P.

The polymerization in (iii) is preferably a suspension polymerization. The term "suspension polymerization" refers to a system in which polymeric precursor molecules that are relatively insoluble in water are suspended as liquid droplets in an aqueous phase. Usually, a suspending agent is employed so as to maintain the suspension, and the resultant polymer is obtained as a dispersed solid phase. While the monomeric building blocks may be directly dispersed in a suspension polymerization system, hydrocarbon solvents or diluents are commonly employed with the monomers, such as n-heptane, isooctane, cyclohexane, benzene, toluene, and the like, including mixtures.

In the suspension polymerization system, a monomer mixture to be polymerized usually comprises the monomers, or, where desired, a polymer-in-monomer solution, the at least one magnetic core (M), solvent and, where employed, an initiator.

Thus, step (iii) preferably comprises:
(iii.1) providing a composition (A) comprising the polymer precursor molecules according to (ii), the at least one magnetic core (M) according to (i), at least one organic solvent, at least one initiator and a water phase and optionally additives, wherein the organic solvent is not miscible with water, and
(iii.2) stirring composition (A) to give an emulsion (B) wherein the emulsion is preferably an organic solvent-in-water emulsion.

Preferably, the polymerization in (iii) is carried out in the presence of an initiator selected from the group consisting of azobis(isobutyronitril) (AIBN), 2,2'-azodi(2-methylbutyronitrile) (VAZO 67), 1,1'-azobis(cyanocyclohexane) (VAZO 88), benzoylperoxid (BPO), 2,2'-azobis(2-amidinopropane) dihydrochloride (AAPH) and 4,4'-azobis(4-cyanopentanoic acid) (ACVA).

The monomers and the at least one magnetic core (M) are preferably suspended in a water solution optionally containing at least one suspending agent. The amount of water employed can vary widely, depending on the type of reactor employed, agitation means, and the like, though the final suspension mixture preferably contains about 5 to 60 percent by weight of the monomeric building blocks based on total weight of the entire mixture including water.

A variety of suspending agents can be employed as additives in suspension polymerization systems, since the method involves a liquid-in-liquid dispersion and affords a final product in the form of discrete solid particles. The suspension agents include insoluble carbonates, silicates, talc, gelatine, pectin, starch, cellulose derivatives, insoluble phosphates, PVA, salts, NaCl, KCl, PVP and the like. Preferably, the polymerization in (iii) is carried out in the absence of any tensides.

The time employed for polymerization should be that sufficient for the degree or extent of conversion desired, and can vary over a wide range, depending on various reaction parameters such as the temperature employed, from a very few minutes to many hours, such as 48 hours. Preferably, step (iii) is carried out for a time in the range of from 1 hour to 30 hours, preferably 1 hour to 8 hours.

Temperatures employed are at least sufficient to effectuate thermal polymerization, or to cause decomposition of the free radical initiator, where used, which provides initiation of the reaction, preferably below temperatures which might cause gel formation of the polymer. Temperatures preferably employed are in the range of about 0° C. to 100° C., preferably 40 to 90° C.

The stirring is preferably carried out with an overhead stirrer.

Preferably, the polymer matrix (P1) comprises a cross-linked polymer, this polymer more preferably being obtained or obtainable by co-polymerizing a polymer with crosslinking agent. Suitable agents for crosslinking polymers are known to those skilled in the art, and include, but are not limited to divinylbenzene, bis(vinylphenyl)ethane, bis(vinylbenzyloxy)hexane, bis(vinylbenzyloxy)dodecane and derivatives of those.

According to a particularly preferred embodiment divinylbenzene is employed as crosslinking agent. Preferably, the polymer matrix (P1) is obtained or obtainable by crosslinking a polymer with 5-90 vol % of a crosslinking agent, based on the total amount of the polymer Step (iv)

The polymer matrix (P1) is hypercrosslinked in step (iv), wherein this hypercrosslinking is carried out via a Friedel-Crafts reaction. The term "Friedel-Crafts reaction" for the purposes of this application, refers to a well-known reaction type developed by Charles Friedel and James Crafts to attach substituents to an aromatic ring by electrophilic aromatic substitution and includes the two main types of Friedel-Crafts reactions: alkylation reactions and acylation reactions. Alkylation may be preferably used in the invention. Such reactions are usually carried out in the presence of a suitable catalyst, such as a Lewis acid.

The hypercrosslinking in (iv) is carried out at a temperature of less than or equal to 80° C., such as a temperature in the range of from −30° C. to 80° C. It has been surprisingly found that such reaction conditions yield in stable hypercrosslinked particles having a high magnetization saturation.

More preferably (iv) is carried out at a temperature of less than 70° C., more preferably at less than 60° C., more preferably at less than 50° C., more preferably at less than 40° C., more preferably at less than 30° C., such as preferably at a temperature in the range of from −30° C. to 30° C., more preferably at a temperature in the range of from −20° C. to 30° C., more preferably at a temperature in the range of from −20° C. to 30° C., more preferably at a temperature in the range of from −10° C. to 30° C., more preferably at a temperature in the range of from 0° C. to 30° C. and most preferably in the range of from 10 to 30° C. During the reaction, the temperature may be varied, constantly or stepwise, or held essentially constant. In case the temperature is varied, it is to be understood that the temperature is always kept at a temperature being equal to or less than 120° C., less than 100° C., less than 80° C., and preferably at a temperature of less than 70° C., more preferably at less than 60° C., more preferably at less than 50° C., more preferably at less than 40° C., more preferably at less than 30° C., such as preferably at a temperature in the range of from −30° C. to 30° C., more preferably at a temperature in the range of from −20° C. to 30° C., more preferably at a temperature in the range of from −20° C. to 30° C., more preferably at a temperature in the range of from −10° C. to 30° C., more preferably at a temperature in the range of from 0° C. to 30° C. and most preferably in the range of from 10 to 30° C.

Preferably, (iv) is carried out in the presence of a catalyst comprising, more preferably consisting of, a Lewis acid selected from the group consisting of $FeCl_3$, $ZnCl_2$, $AlCl_3$, $BF_3$, $SbCl_5$, $SnCl_4$, $TiCl_4$, $SiCl_4$ and mixtures of two or more thereof.

More preferably, the catalyst comprises, more preferably consists of, $FeCl_3$ or $ZnCl_2$ or a mixture thereof.

Optional Step (v)

Besides the steps described above, the method may comprise one or more further steps. In particular, the method may comprise functionalizing the surface of the polymeric particles obtained according to (iii) or (iv).

Thus, the present invention also relates to a method, as described above, as well as to magnetic particles obtained or obtainable by the above-described method, wherein the method further comprises:

(i) functionalizing the surface of the polymer particle according to (iii) or (iv).

Preferably in this step, the polymer particles are functionalized with a group selected from the group consisting of —OH, —COOH, diethylaminoethanol, R—$SO_2$—OH, —$NH_2$, R—$SO_2$—OH, —RNH, —$R_2$N, —$R_3N^+$—$CH_3$, —$C_2H_5$, —$C_4H_9$, —$C_8H_{17}$, —$C_{18}H_{37}$, —$C_6H_5$, —$C_6H_9NO_6$, Phenyl-Hexyl, Bi-Phenyl, Hydroxyapatit, boronic acid, biotin, azide, epoxide, alkyl, aryl, cycloalkyl, heteroaryl, heterocycloalkyl, aminoacids, —COOR, —COR, —OR, antibodies and fragments thereof, aptameres, nucleic acids, polymers and receptor proteins or binding domains thereof.

Methods for functionalizing polymeric particles are known to the skilled person and are e.g. described in Bioconjugate Techniques $2^{nd}$ Edition, G. T. Hermanson, the disclosure contents of which are hereby incorporated by reference.

Preferably this step comprises at least the treatment of the particles with a suitable base (OH functionalization), such as e.g. KOH. Alternatively, functionalization can be a COOH-functionalization, a Cx-functionalization or an Epoxy-functionalization. Further details on said functionalizations are also given in the accompanying Examples, below.

In light of the foregoing, the present invention preferably relates to a method, as described above, as well as to particles obtained or obtainable by said method, the method comprising:

(i) providing at least one magnetic core (M), preferably at least two magnetic cores (M),
(ii) providing polymer precursor molecules,
(iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and
(iv) hypercrosslinking the polymer matrix (P1) of the polymer particle obtained in (iii) via a Friedel-Crafts reaction, wherein the reaction is carried out at a temperature equal to or less than 80° C., and wherein the Friedel-Crafts reaction is carried out in the presence of a catalyst comprising, more preferably consisting of, $FeCl_3$ or $ZnCl_2$ or a mixture thereof,
to give the magnetic particle.

The crosslinking may be carried out by any suitable solvent known to those skilled in the art and is preferably carried out in a solvent comprising dichloroethane, toluene, acetonitrile, DMF, ethylether, THF, benzene, xylene, dioxane, alkanes, dichloromethane, chloroform, chlorobenzene, carbon tetrachloride, NMP, dichlorobenzenes, trichlorobenzenes, ethers, cycloalkanes, organic halides or mixtures of two or more thereof. More preferably, the crosslinking in (iv) is carried out in a solvent selected from the group consisting of dichloroethane, toluene, acetonitrile, DMF, ethylether, THF, benzene, xylene, dioxane, alkanes, dichloromethane, chloroform, chlorobenzene, carbon tetrachloride, Preferably, the reaction in (iv) is not carried out in dichloroethane or other organic halides, More preferably, the reaction in (iv) is not carried in a solvent comprising dichloroethane or other organic halides.

In particular, the reaction in (iv) is carried out in a solvent comprising at least THF, acetonitrile, DMF, dioxane or toluol. More preferably, (iv) is carried out in a solvent selected from the group consisting of THF, acetonitrile, DMF, dioxane, toluol and mixtures of two or more thereof.

Preferably, the reaction in (iv) is carried out for a reaction time of 4 h or less, such as for a time in the range of from 10 min to 2 h, more preferably 30 min to 1.5 h, more preferably 45 min to 1 h.

Thus, the present invention preferably relates to a method, as described above, as well as to particles obtained or obtainable by said method, the method comprising:
(i) providing at least one magnetic core (M), preferably at least two magnetic cores (M),
(ii) providing polymer precursor molecules,
(iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and
(iv) hypercrosslinking the polymer matrix (P1) of the polymer particle obtained in (iii) via a Friedel-Crafts reaction, wherein the reaction is carried out at a temperature equal to or less than 80° C., and wherein the Friedel-Crafts reaction is carried out for a reaction time of 4 h or less, and preferably in the presence of a catalyst comprising, more preferably consisting of, $FeCl_3$ or $ZnCl_2$ or a mixture thereof,
to give the magnetic particle.

Preferably, the reaction in (iv) is carried out under inert atmosphere, even more preferably during the reaction in (iv) an inert gas is streamed through the reaction mixture. Preferably, the inert gas is nitrogen and/or argon. The term "during the reaction in (iv)" is denoted to mean that preferably for a time in the range of from 10 min to 2 h, more preferably during the whole reaction time, the inert gas is streamed through the mixture. The "streaming" is carried out e.g. by bubbling the inert gas through the mixture. Suitable methods are known to the skilled person.

Thus, the present invention preferably relates to a method, as described above, as well as to particles obtained or obtainable by said method, the method comprising:
(i) providing at least one magnetic core (M), preferably at least two magnetic cores (M),
(ii) providing polymer precursor molecules,
(iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and
(iv) hypercrosslinking the polymer matrix (P1) of the polymer particle obtained in (iii) via a Friedel-Crafts reaction, wherein the reaction is carried out at a temperature equal to or less than 80° C., and wherein the Friedel-Crafts reaction is preferably carried out for a reaction time of 4 h or less, and preferably in the presence of a catalyst comprising, more preferably consisting of, $FeCl_3$ or $ZnCl_2$ or a mixture thereof, and wherein during the reaction an inert gas is streamed through the reaction mixture,
to give the magnetic particle.

Preferably in (iv), the at least magnetic core (M) is embedded into the matrix.

Use/Method of Analyzing

The magnetic particle described above and the magnetic particles obtainable or obtainable by the method described above are preferably used for qualitative and/or quantitative determination of at least one analyte in a fluid.

The term "qualitative" determination as used herein refers to determining the presence or absence of at least one analyte in the fluid. Moreover, the term may also encompass an assessment of the nature of the analyte, i.e. it may encompass the identification of the analyte or the identification of a class of chemical molecules to which the analyte belongs.

The presence or absence of the at least one analyte can be determined by contacting the fluid sample to the magnetic particles for a time and under conditions sufficient to allow for binding of the at least one analyte to the magnetic particle, subsequently removing the remaining fluid sample from the magnetic particle and determining whether the at least one analyte was bound to the magnetic particle, or not. In order to determine whether the analyte was bound to the magnetic particle, or not, compounds bound to the particle may be eluted by suitable techniques and the presence or absence of the at least one analyte may be subsequently determined in the eluate. Alternatively, the binding at least one analyte may be determined directly, i.e. bound to the magnetic particle.

The identification of the at least one analyte or the chemical class to which it belongs may be done after the said analyte has been eluted from the magnetic particle by suitable analytical methods such as mass spectrometry, UV-vis, NMR, IR or biochemical methods, such as ELISA, RIA and the like. Alternatively, depending on the kind of agent used for the surface functionalization, only a specific analyte may be bound. For example, in the case of antibodies, the chemical nature of the analyte is predetermined due to the antibody's specificity.

The term "quantitative" as used herein refers to determining the absolute or relative amount of the at least one analyte comprised in a fluid sample.

The amount of the at least one analyte can be determined as described above for the qualitative determination. However, after elution of the analyte from the magnetic particles, the amount is to be determined in the eluate. Alternatively, the amount of bound analyte may be determined directly.

In light of the above, the present invention also contemplates a method for determining at least one analyte in a fluid sample comprising the steps of:
(a) contacting a magnetic particle according to the invention or the magnetic particle obtained or obtainable by the method of the present invention with a fluid sample comprising or suspected to comprise the at least one analyte; and
(b) determining the at least one analyte eluted from the said magnetic particle.

Typically, the determination referred to in this context is a qualitative or quantitative determination.

Typically, step (a) of the method is carried out for a time and under conditions sufficient to allow for binding of the at least one analyte to the magnetic particle. Thus, preferably in step (a) at least a portion, preferably all of, the analyte is bounded to the particle. In case, the determination is a quantitative determination, preferably substantially all of the analyte present in the fluid sample is bound to the particle.

Preferably, step (a) further comprises step:
(a1) washing the magnetic particle to which at least a portion of the at least one analyte is bounded to, preferably under conditions which do not elute the at least one analyte; and/or
(a2) eluting the at least one analyte from the magnetic particle under conditions suitable to allow the elution of the at least one analyte.

More specifically, the qualitative or quantitative determination in (b) may comprise the determination of the presence or absence of bound analyte on the magnetic particle or the determination of the amount of analyte bound to the magnetic particle.

It is to be understood that the washing step in (a1) may be carried as single washing step. Alternatively, more than one washing step may be carried out.

More specifically, the qualitative determination may comprise the following further step as part of step (a) and/or (b):
determining whether the at least one analyte was bound to the magnetic particle, or not.

Using the magnetic particles of the invention or obtainable by the method of the invention, advantageously reduces the matrix carry-over of the said fluids in applications as discussed above.

Analytes to be determined by the magnetic particles of the invention or the magnetic particles obtained by the method of the invention or analytes to be determined in accordance with the aforementioned uses are, preferably, chemical compounds present in biological fluid samples, environmental samples or solutions of mixtures of chemical compounds. Accordingly, the fluid sample referred to in accordance with the present invention is, preferably, selected from the group of fluids consisting of: body fluids, liquid or dissolved environmental samples and solutions of mixtures of chemical compounds.

In a preferred embodiment the fluid sample as used herein refers to a biological sample obtained for the purpose of evaluation in vitro. In the methods of the present invention, the fluid sample or patient sample preferably may comprise any body fluid.

Preferred fluid samples are whole blood, serum, plasma, bronchioalveolar lavage (BAL), epithelial lining fluid (ELF), urine or sputum, with plasma or serum being most preferred.

The term fluid sample includes biological samples that have been manipulated in any way after their procurement, such as by treatment with reagents, solubilization, or enrichment for certain components, such as proteins or polynucleotides. Typically, the fluid sample is a liquid sample.

The fluid sample may for example be whole blood, serum, antibodies recovered from the patient or plasma. The fluid sample is preferably whole blood, serum or plasma. In one embodiment, the sample is a clinical sample. In another embodiment, the sample is used in a diagnostic assay.

Depending on the nature of the fluid sample, different classes of chemical compounds are to be detected. Preferably, the analyte in accordance with the present invention may be selected from the group of steroids, sugars, vitamins, drugs including medicaments and drugs for abuse, organic compounds, proteins, nucleic acids and mixtures of two or more thereof. Such analytes, pivotally, occur in biological samples. However, they may also be present in environmental samples.

The aforementioned applications for determining analytes in fluid samples may, preferably, be applied or are involved in diagnostic purposes, drug of abuse testing, environmental control, food safety, quality control, purification or manufacturing processes. In diagnostic applications, the qualitative or quantitative determination of an analyte may allow aiding the diagnosis if the analyte is, e.g., a biomarker for a disease or medical condition. Similarly, the qualitative or quantitative assessment of an analyte being an indicator for environmental changes may help to identify pollution or to make assessments of environmental changes. Food safety as well as manufacturing or purification processes may be controlled by qualitative or quantitative determination of indicator analytes. Such indicators may also be determined in connection with general aspects of quality control, e.g., also in storage stability assessments of products and the like.

Preferably, the analyte is determined by mass spectrometry, UV-vis, NMR, IR.

Summarizing the findings of the present invention, the following embodiments are particularly preferred:
1. A method of preparing a magnetic particle comprising a polymer matrix (P) and at least one magnetic core (M), preferably at least two magnetic cores (M), wherein the polymer matrix (P) comprises at least one hypercrosslinked polymer, wherein the method comprises:
   (i) providing at least one magnetic core (M), preferably, at least two magnetic cores (M),
   (ii) providing polymer precursor molecules,
   (iii) polymerizing the polymer precursor molecules according to (ii) in the presence of the at least one magnetic core (M), thereby forming a particle comprising the at least one magnetic core (M), preferably the at least two magnetic cores (M), embedded in a polymer matrix (P1), and
   (iv) hypercrosslinking the polymer matrix (P1) of the polymer particle obtained in (iii) via a Friedel-Crafts reaction, wherein the reaction is carried out at a temperature equal to or less than 80° C.,
to give the magnetic particle.
2. The method of embodiment 1, wherein the reaction in (iv) is carried out at a temperature equal to or less than 30° C.
3. The method of embodiment 1 or 2, wherein the reaction in (iv) is carried out for a reaction time of 2 h or less.

4. The method of any one of embodiments 1 to 3, wherein the reaction in (iv) is not carried out in a solvent comprising dichloroethane or other organic halides.
5. The method of any one of embodiments 1 to 4, wherein the reaction in (iv) is carried out in a solvent comprising at least THF, acetonitrile, DMF, dioxane or toluol.
6. The method of any one of embodiments 1 to 5, wherein the reaction in (iv) is carried out in a solvent selected from the group consisting of THF, acetonitrile, DMF, dioxane, toluol and mixture of two or more thereof.
7. The method of any one of embodiments 1 to 6, wherein the reaction in (iv) is carried out under inert atmosphere.
8. The method of any one of embodiments 1 to 7, wherein during the reaction in (iv) an inert gas is streamed through the mixture.
9. The method of any one of embodiments 1 to 8, wherein in (iv) the at least magnetic core (M) is embedded into the matrix.
10. The method of any one of embodiments 1 to 9, wherein the hypercrosslinking in (iv) is carried out in the presence of a catalyst selected from the group consisting of a Lewis acid, preferably selected from the group consisting of $FeCl_3$, $ZnCl_2$, $AlCl_3$, $BF_3$, $SbCl_5$, $SnCl_4$, $TiCl_4$, $SiCl_4$ and mixtures of two or more thereof, more preferably $FeCl_3$ or $ZnCl_2$, or a mixture thereof.
11. The method of any one of embodiments 1 to 10, wherein the method further comprises:
   (v) functionalizing the surface of the polymer particle according to (iv).
12. The method of embodiment 11, wherein in step (v), the polymer particle is functionalized with a group selected from the group consisting of —OH, —COOH, diethylaminoethanol, R—$SO_2$—OH, —$NH_2$, R—$SO_2$—OH, —RNH, —$R_2$N, —$R_3N^+$—$CH_3$, —$C_2H_5$, —$C_4H_9$, —$C_8H_{17}$, —$C_{18}H_{37}$, —$C_6H_5$, $C_6H_9NO_6$ Phenyl-Hexyl, Bi-Phenyl, Hydroxyapatit, boronic acid, biotin, azide, epoxide, alkyl, aryl, cycloalkyl, heteroaryl, heterocycloalkyl, aminoacids, —COOR, —COR, —OR, antibodies and fragments thereof, aptameres, nucleic acids, and receptor proteins or binding domains thereof.
13. The method of any one of embodiments 1 to 12, wherein the polymerization in (iii) is a suspension polymerization.
14. The method of any one of embodiments 1 to 13, wherein the polymerization in (iii) is carried out in the presence of an initiator selected from the group consisting of Azobis (isobutyronitril) (AIBN), 2,2'-Azodi(2-methylbutyronitrile) (VAZO 67), 1,1'-Azobis(cyanocyclohexane) (VAZO 88), benzoylperoxid (BPO), 2,2'-Azobis(2-amidinopropane) dihydrochloride (AAPH) and 4,4'-Azobis(4-cyanopentanoic acid) (ACVA)
15. The method of any one of embodiments 1 to 14, wherein step (iii) comprises:
   (iii.1) providing a composition (A) comprising the polymer precursor molecules according to (ii), the at least one magnetic core (M) according to (i), at least one organic solvent, at least one initiator and a water phase, wherein the organic solvent is not miscible with water, and
   (iii.2) stirring composition (A) to give an emulsion (B), wherein the emulsion is preferably an organic solvent-in-water emulsion.
16. The method of embodiment 15, wherein the stirring is carried out with an overhead stirrer.
17. The method of any one of embodiments 1 to 16, wherein the polymerization in (iii) is carried out in the absence of any tensides.
18. The method of any one of embodiments 1 to 17, wherein step (iii) is carried out for a time in the range of from 1 h to 30 h, preferably 1 h to 8 h.
19. The method of any one of embodiments 1 to 18, wherein step (iii) is carried out at a temperature in the range of from 0° C. to 100° C., preferably 40° C. to 90° C.
20. The method of any one of embodiments 1 to 19, wherein step (i) comprises:
   (i.1) providing at least one magnetic nanoparticle, and
   (i.2) coating the at least one nanoparticle with a coating C1, the coating C1 preferably being selected from a group consisting of tensides, silica, silicates, silanes, phosphates, phosphonates, phosphonic acids and mixtures of two or more thereof
to give the magnetic core (M).
21. The method of embodiment 20, wherein the magnetic core (M) in (i.1), comprises, preferably consists of, at least one magnetic, preferably superparamagnetic, nanoparticle and optionally a coating C2.
22. The method of embodiment 21, wherein (i) comprises:
   (i.1.1) providing more than 20 nanoparticles and, preferably, at least 21 nanoparticles with at least one coating C2,
   (i.1.2) aggregating the more than 20 nanoparticles, thereby forming a supraparticle, and
   (i.1.3) optionally coating the supraparticle according to (i.2) with at least one coating C1,
to give the at least one magnetic core (M).
23. The method of embodiment 22, wherein the at least one coating C2 is selected from the group consisting of tricarboxylic acids, tricarboxylic acid salts, tricarboxylic derivatives, amino acids, amino acid salts, amino acid derivatives, surfactants, salt of surfactants, fatty acids, fatty acid salts and fatty acid derivatives.
24. Magnetic particle obtained or obtainable by a method of any one of embodiments 1 to 23.
25. Magnetic particle of embodiment 24, wherein the magnetic particle has a saturation magnetization of at least 1 A m$^2$/kg, preferably of at least 10 A m$^2$/kg, as determined according to ASTM A 894/A 894M.
26. Magnetic particle of any one of embodiments 24 to 25, wherein the magnetic particle has a particle size in the range of from 1 to 60 micrometers, as determined according to ISO 13320.
27. Magnetic particle of any one of embodiments 24 to 26, wherein the polymer matrix comprises pores having a pore size smaller than 100 nm, preferably smaller or equal to 50 nm, as determined according to ISO 15901-3.
28. Magnetic particle of any one of embodiments 24 to 27, wherein at least 90% of all pores present in the polymer matrix (P) have a pore size smaller than 10 nm and at least 50% of all pores present in the polymer matrix have a pore size smaller than 5 nm, as determined according to ISO 15901-3, preferably, wherein the polymer matrix (P) does not comprise macropores having a pore size larger than 50 nm.
29. Magnetic particle of any one of preceding embodiments 24 to 28, wherein the particle has a BET specific surface area in the range of from 50 to 2500 m$^2$/g, as determined according to ISO 9277.
30. Magnetic particle of any one of embodiments 24 to 29, wherein the at least one magnetic core (M) comprises a compound selected from the group consisting of metal, metal carbide, metal nitride, metal sulfide, metal phosphide, metal oxide, metal chelate and a mixture of two or more thereof.

31. Magnetic particle of any one of embodiments 24 to 30, wherein the at least one magnetic core (M) comprises a metal oxide or a metal carbide, more preferably, an iron oxide, in particular an iron oxide selected from the group consisting of $Fe_3O_4$, $\alpha$-$Fe_2O_3$, $\gamma$-$Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3, more preferably 2, and wherein y is preferably 3 or 4 most preferably, $Fe_3O_4$.

32. Magnetic particle of any one of embodiments 24 to 31, wherein the magnetic particle is superparamagnetic.

33. Magnetic particle of any one of embodiments 24 to 32, wherein the at least one magnetic core (M) comprises at least one magnetic nanoparticle, preferably at least one iron oxide nanoparticle, more preferably a $Fe_3O_4$-nanoparticle.

34. Magnetic particle of any one of embodiments 24 to 33, wherein said at least one magnetic core (M) comprises, more preferably consists of a magnetic nanoparticle and a coating C1.

35. Magnetic particle of embodiment 32, wherein the at least one magnetic nanoparticle has a diameter in the range of from 1 to 20 nm, preferably 4 to 15 nm, as determined according to TEM-measurements.

36. Magnetic particle of any one of embodiments 24 to 33, wherein the at least one magnetic core (M) comprises, preferably consists of, a supraparticle and, optionally, comprising a coating C1.

37. Magnetic particle of embodiment 36, wherein said supraparticle consists of aggregated nanoparticles and, preferably, of more than 20 aggregated nanoparticles and, more preferably, of between 100 and 1.5 million nanoparticles.

38. The magnetic particle of embodiment 37, wherein each nanoparticle is coated with at least one coating C2, which coating preferably is deposited on the surface of the nanoparticle, and wherein the coating C2 is preferably selected from the group consisting of dicarboxylic acids, dicarboxylic acid salts, dicarboxylic acid derivatives, tricarboxylic acids, tricarboxylic acid salts, tricarboxylic derivatives, amino acids, amino acid salts, amino acid derivatives, surfactants, salt of surfactants, polyacrylic acid, polyacrylic acid salts, polyacrylic acid derivatives, fatty acids, fatty acid salts and fatty acid derivatives.

39. Magnetic particle of any one of embodiments 36 to 38, wherein the supraparticle including the at least one coating C2, has a diameter in the range of from 80 to 500 nm, preferably 150 to 400 nm, and most preferably 200 to 300 nm, as determined according to DLS.

40. Magnetic particle of embodiment 39, wherein the at least one coating C1 selected from the group consisting of tensides, silica, silicates, silanes, phosphates, phosphonates, phosphonic acids and mixtures of two or more thereof.

41. Magnetic particle of any one of embodiment 34 to 40, wherein the coating C1 is selected from the group consisting of silica, tetraethyl orthosilicate, 3-(trimethoxysilyl)propyl methacrylate, vinyltrimethoxysilane, vinyltriethoxysilane, allyltrimethoxysilane, allyltriethoxysilane, triethoxyvinylsilane, 3-(trimethoxysilyl)propyl acrylate, trimethoxy(7-octen-1-yl) silane, trimethoxymethylsilane, triethoxymethylsilane, ethyltrimethoxysilane, triethoxy (ethyl)silane, trimethoxyphenylsilane, trimethoxy(2-phenylethyl)silane trimethoxy(propyl)silane, n-propyltriethoxysilane, isobutyl(trimethoxy)silane, isobutyltriethoxysilane, vinylphosphonic acid, dimethyl vinylphosphonate, diethyl vinylphosphonate, diethyl allylphosphonate, diethyl allyl phosphate, diethyl (2-methylallyl)phosphonate, octylphosphonic acid, butylphosphonic acid, decylphosphonic acid, hexylphosphonic acid, hexadecylphosphonic acid, n-dodecylphosphonic acid, lauric acid, myristic acid, palmitic acid, stearic acid, and arachidic acid, propionic acid, butyric acid, valeric acid, caproic acid, enanthic acid, caprylic acid, pelargonic acid, capric acid, undecylic acid, tridecylic acid, pentadecylic acid, margaric acid, nonadecylic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, oleic acid, linoleic acid, linolenic acid, arachidonic acid, hexadecatrienoic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, calendic acid, eicosadienoic acid, docosadienoic acid, adrenic acid, docosapentaenoic acid, tetraco-satetraenoic acid, tetracosapentaenoic acid, 5-dodecenoic acid, 7-tetradecenoic acid, pal-mitoleic acid, vaccenic acid, paullinic acid, 15-docosenoic acid, 17-tetracosenoic acid, elaidic acid, gondoic acid, mead acid, erucic acid, nervonic acid, rumenic acid, calendic acid, jacaric acid, eleostearic acid, catalpic acid, punicic acid, rumelenic acid, parinaric acid, bosseopentaenoic acid, pinolenic acid, podocarpic acid and mixtures of two or more thereof.

42. Magnetic particle of any one of embodiments 34 to 41, wherein the coating C1 is preferably a tenside or silica coating 43. Magnetic particle of any one of embodiments 34 to 42, wherein the at least one magnetic core (M) comprises the coating C1 in an amount of from 1 to 40% by weight, preferably from 2 to 15% by weight, more preferably from 5 to 10% by weight, based on the total weight of at least one magnetic core (M).

44. Magnetic particle of any one of embodiments 34 to 43, wherein the coating C1 is a tenside, and wherein the at least one magnetic core (M) preferably comprises the coating C1 in an amount of from 1 to 15% by weight, preferably from 5 to 10% by weight, based on the total weight of at least one magnetic core (M), preferably an oleic acid coating.

45. Magnetic particle of embodiment 34 to 44, wherein the coating C1 comprises vinyl or acryl groups.

46. Magnetic particle of any one of embodiments 24 to 45, wherein the particle comprises at least two magnetic cores (M)

47. Magnetic particle of any one of embodiments 24 to 46, wherein the particle is a substantially spherical particle.

48. Use of the magnetic particle of any one of embodiments 1 to 47 for qualitative and/or quantitative determination of at least one analyte in a fluid.

49. The use of the preceding embodiment, wherein the said analyte is selected from the group of steroids, sugars, vitamins, drugs, organic compounds, proteins, nucleic acids, sugars and mixtures of two or more thereof.

50. The use of embodiment 48 or 49, wherein the said analyte is enriched by the magnetic particles obtainable by the method of any one of embodiments 1 to 23 or a magnetic particle of any one of embodiments 24 to 46.

51. The use of any one of embodiments 48 to 50, wherein the said analyte is determined by mass spectrometry, UV-vis, NMR, IR.
52. The use of any one of embodiments 48 to 52, wherein said fluid is selected from the group of fluids consisting of: body fluids, liquid or dissolved environmental samples and solutions of mixtures of chemical compounds.
53. The use of embodiment 52, wherein the magnetic particle of any one of embodiments 1 to 23 or the magnetic particle according to any one of embodiment 24 to 46 reduces the matrix carry-over of the said fluids.
54. The use of embodiment 53, wherein said qualitative and/or quantitative determination of the at least one analyte in a fluid is involved in diagnostic purposes, drug of abuse testing, environmental control, food safety, quality control, purification or manufacturing processes.
55. A method for determining at least one analyte in a fluid sample comprising the steps of:
   a) contacting a magnetic particle of the invention or a magnetic particle obtained by the method of the present invention with a fluid sample comprising or suspected to comprise the at least one analyte; and
   b) determining the at least one analyte bound to the said magnetic particle.
56. The method of embodiment 55, wherein step a) of the method is carried out for a time and under conditions sufficient to allow for binding of the at least one analyte to the magnetic particle.
57. The method of embodiments 55 or 56, wherein step a) further comprises:
   a1) washing the magnetic particle to which at least a portion of the at least one analyte is bounded to, preferably under conditions which do not elute the at least one analyte; and/or
   a2) eluting the at least one analyte from the magnetic particle under conditions suitable to allow the elution of the at least one analyte.
58. The method of any one of embodiments 55 to 57, wherein said determination comprises the determination of the presence or absence of bound analyte on the magnetic particle or the determination of the amount of analyte bound to the magnetic particle.

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

All references cited throughout this specification are herewith incorporated by reference with respect to the specifically mentioned disclosure content as well as in their entireties.

EXAMPLES

The following Examples shall merely illustrate the invention. Whatsoever, they shall not be construed as limiting the scope of the invention.

Example 1: Preparation of Beads

Silica-Coated Magnetic Nanoparticles (1)
In a general procedure 43 g $FeCl_2.4H_2O$ (0.22 mol) and 70 g $FeCl_3$ (0.43 mol) were added under stirring to 2 L water and heated to 70° C. 125 mL $NH_4OH$ (28% in $H_2O$) were added and after 10 min the black precipitate was separated with a magnet. The supernatant was discarded and the magnetic nanoparticles were washed five times with water. The nanoparticles were resuspended in 2 L ethanol under ultrasonication and transferred in a 4 L reactor. The total volume was filled to 3.2 L with ethanol and under stirring a mixture of tetraethoxysilane (TEOS; 50 mL; 0.22 mol) and ethanol (350 mL) was added drop wise. After 24 h stirring at 25° C. the nanoparticles were separated with a magnet and the supernatant was discarded. The TEOS coated nanoparticles were washed three times with ethanol and resuspended in 2 L ethanol under ultrasonication. The nanoparticles were transferred in a 4 L reactor and the total volume was filled to 3.1 L with ethanol. The mixture was heated to 50° C. and under stirring a mixture of [3-(methacryloyloxy)propyl]trimethoxysilane (MEMO; 77 mL; 0.32 mol), isobutyl(trimethoxy)silane (ISO; 33 mL; 0.17 mol) and ethanol (390 mL) was added drop wise. After 24 h stirring at 50° C. the nanoparticles were separated with a magnet and the supernatant was discarded. The MEMO/ISO coated nanoparticles were washed two times with ethanol and stored in ethanol to give silica-coated magnetic nanoparticles (1) (50 g).

Tenside-Coated Magnetic Nanoparticles (2)
In a general procedure 126 g $FeCl_2.4H_2O$ (0.63 mol) and 248 g $FeCl_3$ (1.53 mol) were added under stirring to 3 L water and heated to 55° C. 460 mL $NH_4OH$ (28% in $H_2O$) were added and after 15 min the black precipitate was separated with a magnet. The supernatant was discarded and the magnetic nanoparticles were washed three times with water. The magnetic nanoparticles were resuspended in 2000 mL and the pH was adjusted to 7-9 with NaOH (10 M). After ultrasonication for 30 min the suspension was transferred in a 4 L reactor and 1 L water was added. While stirring 120 mL oleic acid were added and the suspension was stirred for 45 min at 25° C. The magnetic nanoparticles were separated with a magnet and the supernatant was discarded. The tenside-coated nanoparticles were washed three times with water and ethanol and stored in ethanol to give tenside-coated magnetic nanoparticles (2) (203 g).

Silica-Coated Magnetic Supraparticles (3)
In a general procedure 44 g $FeCl_3.6H_2O$ (0.16 mol) were dissolved in 800 mL ethylene glycol and transferred to high pressure reactor. 9.7 g sodium citrate (0.037 mol) and 51.9 g sodium acetate (0.63 mol) were added and the high pressure reactor was sealed. The mixture was treated with stirring at 160° C. for 2 h and at 200° C. for 18 h. The formed nanoparticles were separated with a magnet and the supernatant was discarded. The magnetic nanoparticles were washed three times with ethanol and five times with water to give magnetic supraparticles (13.3 g). 10 g of the supraparticles were resuspended in 1500 mL ethanol in a 2 L reactor under ultrasonication and while stirring a mixture of tetraethoxysilane (TEOS; 15 mL; 68 mmol) and ethanol (50 mL) was added drop wise. After 20 h stirring at 25° C. the supraparticles were separated with a magnet and the supernatant was discarded. The TEOS coated supraparticles were washed two times with ethanol and resuspended in 1300 mL ethanol under ultrasonication. The mixture was heated to 65° C. and under stirring a mixture of [3-(methacryloyloxy)propyl]trimethoxysilane (MEMO; 14 mL; 59 mmol), isobutyl(trimethoxy)silane (ISO; 6 mL; 31 mmol) and ethanol (180 mL) was added drop wise. After 16 h stirring at 50° C. the supraparticles were separated with a magnet and the supernatant was discarded. The MEMO/ISO coated supraparticles were washed three times with ethanol and stored in ethanol to give silica-coated magnetic supraparticles (3) (10 g).

Magnetic Polymer Particles (4)

In a general procedure 650 mL water was added to a 2 L glass reactor with mechanical stirrer. 13.5 g PVA was added and stirred until complete solution. 10 g of (1), (2) or (3) were separated with a magnet and the supernatant was discarded. The magnetic nanoparticles were washed one time with toluene and then resuspended in 168 mL toluene. 23.6 mL divinylbenzene (0.17 mol) and 23.6 mL vinylbenzyl chloride (0.17 mol) were added and the mixture was ultrasonicated for 1 h. 3.84 g 2,2'-azobis(2-methylbutyronitrile) (20 mmol) were added and the mixture was transferred to the PVA-solution under rapid stirring. The mixture was heated to 80° C. and the reaction continued for 4 h. The formed magnetic polymer particles were separated with a magnet and the supernatant was discarded. The particles were washed three times with water and methanol and resuspended in isopropanol/water (10/90 v/v) to give magnetic polymer particles (4) (52.3 g).

Porous Magnetic Polymer Particles (5)

In a general procedure 5 g of (4) were separated with a magnet and the supernatant was discarded. The magnetic nanoparticles were washed three times with the hypercrosslinking solvent (dichloroethane, toluene, DMF, MeCN, dioxane or THF) and then resuspended in 60 mL in the chosen solvent. The suspension was stirred for 30 min and then heated to 80° C. When the temperature was reached the catalyst ($FeCl_3$ or $ZnCl_2$; 12 mmol) was added and nitrogen was bubbled through the suspension. After 1 h the particles were separated with a magnet and the supernatant was discarded. The particles were washed five times with ethanol to give porous magnetic polymer particles (5) (4.8 g).

OH-Functionalized Porous Magnetic Polymer Particles (6)

In a general procedure 4.8 g of (5) were used as synthesized and suspended in 60 mL KOH-solution (6 M in $H_2O$). The suspension was stirred at 60° C. for 16 h. The particles were separated with a magnet and the supernatant was discarded. The particles were washed several times with water until pH 7 was reached to give OH-functionalized porous magnetic polymer particles (6) (4.8 g).

COOH-Functionalized Porous Magnetic Polymer Particles (7)

In a general procedure 1 g of (6) were used as synthesized and suspended in 20 mL NaClO-solution (10-15% available chlorine in $H_2O$). The suspension was stirred at 60° C. for 1.5 h. The particles were separated with a magnet and the supernatant was discarded. The particles were washed three times with water to give COOH-functionalized porous magnetic polymer particles (7) (1 g).

$C_x$-Functionalized Porous Magnetic Polymer Particles (8)

In a general procedure 1 g of (7) were used as synthesized and washed two times with MES-buffer (2-morpholin-4-ylethanesulfonic acid; 0.1 M; pH 5.0). The particles were resuspended in 40 mL MES-buffer (0.1 M; pH 5.0) and 6.6 mL EDC-solution (3-(ethyliminomethyleneamino)-N,N-dimethylpropan-1-amine; 10% w/w in $H_2O$) and 39.6 mL sulfo-NHS-solution (N-hydroxysulfosuccinimide; 0.03 M in $H_2O$) were added. The suspension was stirred at 11° C. for 35 min. The particles were separated with a magnet and the supernatant was discarded. The particles were washed two times with MES-buffer and 46 mL of a $C_xH_{2x+1}$—$NH_2$-solution (x=4, 6, 8 or 10; 1/6 v/v in ethanol) and 49.5 mL potassium phosphate-buffer (0.1 M; pH 7.5) were added. The suspension was stirred at 25° C. for 2.5 h. The particles were separated with a magnet and the supernatant was discarded. The particles were washed three times with ethanol and two times with potassium phosphate-buffer (0.02 M; pH 7.0) to give $C_x$-functionalized porous magnetic polymer particles (8) (1 g).

Epoxy-Functionalized Porous Magnetic Polymer Particles (9)

In a general procedure 1 g of (6) were used as synthesized and suspended in 10 mL DMF. 20 mL epichlorohydrin and 10 mL NaOH-solution (3.5 M in $H_2O$) were added. The Suspension was stirred at 40° C. for 22 h. The particles were separated with a magnet and the supernatant was discarded. The particles were washed several times with water to give epoxy-functionalized porous magnetic polymer particles (9) (1 g).

The following Particles were prepared:

TABLE 1

Hypercrosslinking examples

| Bead | Solvent | Lewis Acid | Time | Temperature | MS | Change MS | BET |
|---|---|---|---|---|---|---|---|
| 01-03 | | | Before hypercrosslinking | | 11.8 | — | — |
| 01-03-C01A1 | DCE | FeCl3 | 0.5 h | 80° C. | 10.10 | −14% | — |
| 01-03-C01A2 | DCE | FeCl3 | 1 h | 80° C. | 9.21 | −22% | — |
| 01-03-C01A3 | DCE | FeCl3 | 4 h | 80° C. | 1.02 | −91% | — |
| 01-03-C13 | Toluol | FeCl3 | 1 h | 80° C. | 7.4 | −37% | 531 |
| 01-03-C14 | THF | FeCl3 | 1 h | 80° C. | 12.1 | +2.5% | 301 |
| 01-03-C15 | MeCN | FeCl3 | 1 h | 80° C. | 12.0 | +1.7% | 307 |
| 01-03-C16 | DMF | FeCl3 | 1 h | 80° C. | 11.0 | −6.8% | 300 |
| 01-09 | | | Before hypercrosslinking | | 8.00 | — | — |
| 01-09-C04 | DCE | FeCl3 | 10 min | 80° C. | 3.40 | −58% | 1040 |
| 01-09-C06 | DCE | FeCl3 | 20 min | 80° C. | 2.20 | −73% | 1192 |
| 01-09-C02 | DCE | FeCl3 | 60 min | 80° C. | 0.05 | −99% | 1172 |
| 04-11 | | | Before hypercrosslinking | | 7.00 | — | — |
| 04-11-C01A1 | DCE | FeCl3 | 0.5 h | 80° C. | 2.20 | −69% | 2478* |
| 04-11-C01A2 | DCE | FeCl3 | 1 h | 80° C. | 1.90 | −73% | 1342 |
| 04-11-C01A3 | DCE | FeCl3 | 4 h | 80° C. | 0.35 | −95% | 1788 |

TABLE 1-continued

Hypercrosslinking examples

| Bead | Solvent | Lewis Acid | Time | Temperature | MS | Change MS | BET |
|---|---|---|---|---|---|---|---|
| 05-22 | | Before hypercrosslinking | | | 10.47 | | |
| 05-22-C01 | DCE | FeCl3 | 17 h | 80° C. no $N_2$ | 6.78 | −35% | 633 |
| 05-22-C02 | DCE | FeCl3 | 17 h | 80° C. | 9.39 | −10% | 627 |
| 33-02 | | Before hypercrosslinking | | | 2.69 | | — |
| 33-02-C05 | MeCN | ZnCl2 | 0.5 h | 80° C. | 3.06 | 14% | 551 |
| 33-02-C06 | Toluol | ZnCl2 | 0.5 h | 25° C. | 3.12 | 16% | 576 |
| 33-02-C08 | MeCN | FeCl3 | 0.5 h | 80° C. | 2.8 | 4% | 551 |
| 33-02-C09 | Toluol | ZnCl2 | 0.5 h | 110° C. | 2.08 | −23% | 581 |
| 33-02-C14 | Toluol | FeCl3 | 0.5 h | 25° C. | 2.90 | 8% | 726 |
| 33-02-C16 | MeCN | ZnCl2 | 0.5 h | 25° C. | 3.30 | 23% | 640 |
| 33-02-C18 | MeCN | FeCl3 | 4 h | 80° C. | 1.11 | −59% | 870 |
| 33-02-C20 | MeCN | FeCl3 | 0.5 h | 25° C. | 2.90 | 8% | 735 |
| 33-02-C22 | Toluol | FeCl3 | 0.5 h | 110° C. | 0.85 | −68% | 686 |
| 33-02-C25 | Toluol | ZnCl2 | 0.5 h | 25° C. | 2.96 | 10% | 753 |
| 33-02-C26 | Toluol | FeCl3 | 0.5 h | 25° C. | 3.28 | 22% | 63 |
| 33-02-C28 | Toluol | FeCl3 | 0.5 h | 110° C. | 1.59 | −41% | 698 |
| 33-02-C29 | MeCN | FeCl3 | 0.5 h | 25° C. | 3.36 | 25% | 715 |
| 33-02-C33 | MeCN | FeCl3 | 0.5 h | 80° C. | 2.63 | −2% | 696 |
| 33-02-C34 | Toluol | ZnCl2 | 0.5 h | 110° C. | 1.63 | −39% | 720 |
| 33-02-C35 | MeCN | ZnCl2 | 0.5 h | 80° C. | 2.96 | 10% | 855 |
| 33-02-C36 | MeCN | ZnCl2 | 0.5 h | 25° C. | 3.12 | 16% | 752 |

Characterization Methods

For particle size analysis a Mastersizer 2000 with Hydro 2000 (Malvern Instruments) was used.

Samples were suspended in water or ethanol prior to measurements.

For surface area and pore size analysis an Autosorb iQ (Quantachrome Instruments) was used. Samples were degased at 95° C. for 12 h under vacuum for activation.

For magnetization measurements a 7404-S Magnetometer (Lake Shores Cryotronics) was used.

One key requirement for the automation of the particles inside the enrichment-workflow-MS technology is a fast magnetic separation (<5 s) for high throughput. Particle size and saturation magnetization are crucial properties. Therefore, particles with high saturation magnetization (>1 A $m^2$ $kg^{-1}$) and large sizes (>2 μm) are required. Additionally, for the robustness of the system, carry-over of particles has to be avoided. Therefore, the particles need to have high magnetization and particle sizes larger than 1 μm.

Figure 5:
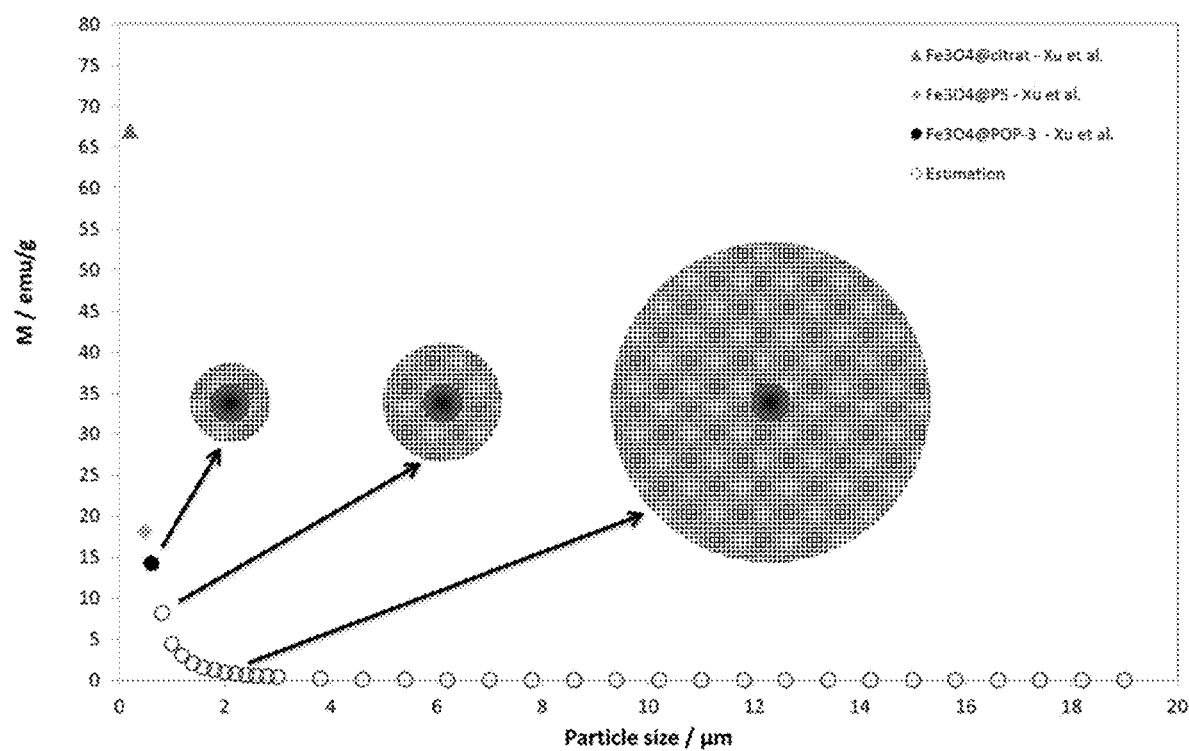
FIG. 5 shows the calculated saturation magnetization for the particles synthesized by Xu et al. with different sizes.

This is the main problem of the just described synthesis routes of magnetic polymer particles. The method of Yang et al. shows the synthesis of small particles (<100 nm) with a low saturation magnetization (4.1 A $m^2$ $kg^{-1}$). These particles do not meet the requirements for automation due to small particle size and low magnetization properties. It is difficult to produce larger particles than 1 μm by emulsion polymerization, giving a low potential of this synthesis method for the production of particles with the required properties. Xu et al. shows the synthesis of small particles (about 400 nm) with a high saturation magnetization (14.1 A $m^2$ $kg^{-1}$). With this method, due to the fact that only one $Fe_3O_4$—NP core is embedded per polymer particle (monocore), larger particles can only be produced by increasing the polymer shell, which would lead to a drastically decrease of the saturation magnetization. FIG. 5 shows the calculated saturation magnetization for the particles synthesized by Xu et al. with different sizes. For example for a synthesis of particles with a size of 2 μm the saturation magnetization would be below 1 A $m^2$ $kg^{-1}$ and for 10 μm lower than 0.01 A $m^2$ $kg^{-1}$. This significant loss of magnetization would lead to extremely long separation times, which are not accepted for high throughput automation. Therefore, these particles do not meet the requirements for automation due to small particle size and mono-core submicron particles synthesis which leads to low magnetization properties.

After polymerization, there is a hypercrosslinking reaction necessary to produce porosity in the particle and therefore high surface areas. One drawback is the building of HCl during this chemical reaction. HCl attacks the $Fe_3O_4$—NPs and therefore lowers the magnetization of the particles. For this reaction step, the coating thickness and the type of coating of the $Fe_3O_4$—NPs are essential. Yang et al. uses coating with oleic acid and Xu et al. protects the $Fe_3O_4$—NPs with citrate.

Example 2: Analyte Capturing Using Magnetic Beads

Analyte Capturing

Figure 6:
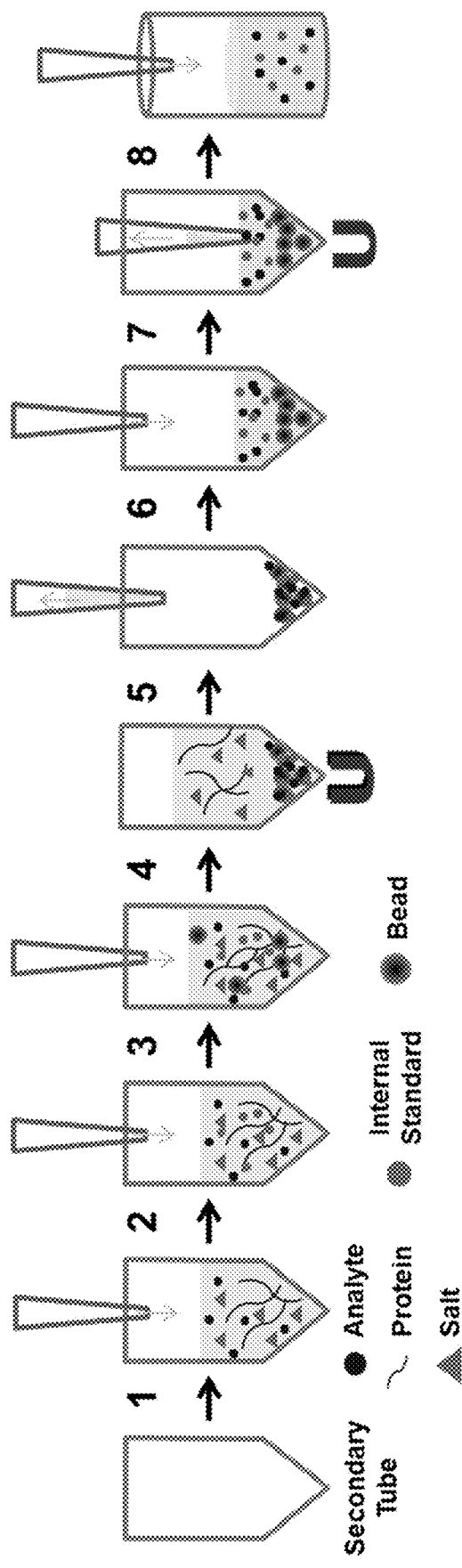
FIG. 6 shows an enrichment workflow using beads as described herein for sample analysis.

For the bead evaluation the beads underwent the enrichment workflow as illustrated in FIG. 6. As test samples a spiked serum pool was used, where the spiked analytes are listed in the following Table 2.

TABLE 2

List of analytes tested with CPS particles

| Steroids | TDMs | DATs | Vitamines |
|---|---|---|---|
| Testosterone | Gabapentin | Methamphetamine | 25OH-VitD$_3$ |
| | Valproic acid | THC | |
| | Cyclosporin | Chlordiazepoxid | |
| | Everolimus | Midazolam | |
| | Gentamicin | Nordiazepam | |
| | Tobramycin | | |

Preparation of Samples

Samples were prepared by spiking the 13 analytes of interest into an analyte-free human serum pool. Internal standard solution was a methanol/water 50:50 v/v mixture containing isotope labelled analogues of the target analytes.

Bead Extraction

For each sample, 100 μL of serum were mixed with 50 μL of bead suspension in water at a concentration of 50 mg/mL and equilibrated for 5 min at room temperature under gentle rolling conditions, so that the analytes could access the entire surface of the particles. In cases where 25OH-Vitamin $D_3$ was analyzed, an additional step was included where 100 μL pre-treatment solution was added to the mixture and incubated for 15 min. The supernatant was then discarded and the magnetic beads washed twice with 200 μL of water. Elution took place with 100 μL acetonitrile/2% formic acid in water 70:30 v/v. In the next step, 80 μL eluate were withdrawn from the vial and transferred to an HPLC vial, where 5 μL internal standard solution were added prior to LC-MS/MS analysis.

Recovery

Quantification was performed by external calibration. For this, a calibration curve was recorded in neat solution. Recovery was calculated by comparing the calculated concentration in the eluate fraction to the spiked amount.

A further aspect to be characterized was the eluate purity regarding residual protein as classified according to:

| Residual protein: | Good | <1.0% | (<855 μg/mL) |
|---|---|---|---|
| | Medium | 1.0-2.0% | (855-1710 μg/mL) |
| | Poor | >2.0% | (>1710 μg/mL) |

For almost all samples the residual protein was below 1% showing good results for the removement of matrix effects.

The following Table 3 shows the capture properties of the different bead types presented above. As can be seen, that with different monomer constitutions, the capture efficiency for different analyte classes changes, giving the possibility of tailored bead design.

The invention claimed is:

1. A method of preparing a magnetic particle comprising a polymer matrix (P) and at least one magnetic core (M), wherein the polymer matrix (P) comprises at least one hypercrosslinked polymer, wherein the method comprises:
    (i) providing at least one magnetic core (M),
    (ii) providing polymer precursor molecules,
    (iii) polymerizing the polymer precursor molecules according to (ii) in the presence of the at least one magnetic core (M), thereby forming a particle comprising the at least one magnetic core (M) embedded in a polymer matrix (Pl), and
    (iv) hypercrosslinking the polymer matrix (Pl) of the polymer particle obtained in (iii) via a Friedel-Crafts reaction, wherein the reaction is carried out at a temperature equal to or less than 80° C.,
    to give the magnetic particle, wherein the magnetic particle has a particle size in the range of from 5 to 40 micrometers,
    wherein the reaction in (iv) is not carried out in a solvent comprising dichloroethane or other organic halides;
    wherein the reaction in (iv) is carried out for a reaction time of 2 h or less;
    wherein the reaction in (iv) is carried out in a solvent comprising at least THF, acetonitrile, DMF, dioxane or toluol;
    wherein the hypercrosslinking in (iv) is carried out in the presence of a catalyst selected from the group consisting of a Lewis acid.

2. The method of claim 1, wherein the reaction in (iv) is carried out at a temperature equal to or less than 30° C.

3. The method of claim 1, wherein the reaction in (iv) is carried out in a solvent selected from the group consisting of THF, acetonitrile, DMF, toluol, dioxane and mixture of two or more thereof.

4. The method of claim 1, wherein the reaction in (iv) is carried out under inert atmosphere.

TABLE 3

| | Capture properties of different beads | | | | | | | | | | | | |
|---|---|---|---|---|---|---|---|---|---|---|---|---|---|
| Bead Type | Genta-micin % | Gaba-pentin % | Metham-phetamine % | Chlordiaz-epoxid % | Valproic acid % | Midazo-lam % | Tobra-mycin % | Nordiazepam % | Cyclo-sporin % | THC % | Evero-limus % | Testos-terone % | VitD % |
| 01-03 | 76% | 10% | 92% | 83% | 14% | 81% | 59% | 76% | 58% | 26% | 54% | 65% | — |
| 01-05 | 78% | 17% | 76% | 71% | 9% | 71% | 59% | 60% | 40% | 13% | 40% | 50% | 4% |
| 01-10 | 87% | 40% | 111% | 100% | 26% | 80% | 38% | 71% | 35% | 8% | 30% | 57% | 0% |
| 04-13 | 91% | 33% | 91% | 81% | 28% | 77% | 75% | 67% | 31% | 10% | 36% | 48% | — |
| 04-12 | 82% | 26% | 90% | 81% | 28% | 77% | 59% | 64% | 35% | 8% | 38% | 49% | 0% |
| 33-02 | 54% | 15% | 81% | 92% | 12% | 80% | 17% | 77% | 50% | 11% | 12% | 68% | — |
| 33-05 | 16% | 4% | 93% | 118% | 4% | 96% | 31% | 99% | 59% | 11% | 25% | 64% | 0% |
| 44-01 | 42% | 11% | 81% | 76% | 13% | 72% | 14% | 67% | 38% | 6% | 5% | 57% | 17%* |
| 50-01 | 34% | 15% | 75% | 70% | 17% | 77% | 19% | 70% | 34% | 8% | 18% | 51% | 2% |
| 05-22 | 50% | 11% | 87% | 41% | 3% | 19% | 46% | 48% | 68% | 12% | 51% | 57% | — |
| 05-26 | 53% | 2% | 87% | 65% | 3% | 30% | 19% | 62% | 74% | 14% | 26% | 60% | 2% |
| 05-27 | 70% | 2% | 94% | 70% | 2% | 35% | 32% | 56% | 38% | 12% | 20% | 52% | 0% |
| 05-36 | 54% | 4% | 81% | 89% | 4% | 37% | 24% | 72% | 30% | 5% | 24% | 9% | 0% |
| 39-01 | 18% | 3% | 82% | 87% | 2% | 79% | 15% | 79% | 58% | 24% | 14% | 68% | 10%* |
| 40-01 | 33% | 13% | 80% | 85% | 13% | 79% | 8% | 79% | 34% | 6% | 7% | 67% | 4%* |
| 42-01 | 46% | 19% | 79% | 82% | 16% | 76% | 13% | 73% | 28% | 4% | 4% | 55% | 19%* |
| 43-01 | 31% | 19% | 64% | 74% | 16% | 66% | 11% | 66% | 22% | 7% | 4% | 51% | 11%* |
| 46-01 | 3% | 1% | 67% | 82% | 2% | 51% | 5% | 72% | 57% | 7% | 16% | 30% | 34%* |
| 48-01 | 28% | 10% | 79% | 73% | 12% | 77% | 19% | 72% | 39% | 9% | 25% | 51% | 4% |
| 49-01 | 38% | 15% | 58% | 53% | 13% | 57% | 12% | 53% | 26% | 7% | 16% | 39% | 0% |
| 51-01 | 44% | 16% | 63% | 50% | 17% | 59% | 20% | 53% | 29% | 5% | 15% | 43% | 2% |
| 20-04 | 60% | 33% | 61% | 47% | 19% | 41% | 57% | 33% | 6% | 3% | 4% | 18% | — |
| 23-02 | 81% | 21% | 94% | 86% | 36% | 70% | 64% | 73% | 36% | 5% | 44% | 49% | — |
| 47-01 | 15% | 4% | 93% | 142% | 5% | 103% | 32% | 107% | 54% | 6% | 32% | 48% | 0% |

5. The method of claim 1, wherein during the reaction in (iv) an inert gas is streamed through the mixture.

6. The method of claim 1, wherein in (iv) the at least one magnetic core (M) is embedded into the matrix.

7. The method of claim 1, wherein the hypercrosslinking in (iv) is carried out in the presence of a catalyst selected from the group consisting of $FeCl_3$, $ZnCl_2$, $AlCl_3$, $BF_3$, $SbCl_5$, $SnCl_4$, $TiCl_4$, $SiCl_4$ and mixtures of two or more thereof.

8. The method of claim 1, wherein the method further comprises:
   (v) functionalizing the surface of the polymer particle according to (iv).

9. The method of claim 1, wherein the polymerization in (iii) is a suspension polymerization.

* * * * *